US007621875B2

(12) United States Patent
Pravica et al.

(10) Patent No.: US 7,621,875 B2
(45) Date of Patent: Nov. 24, 2009

(54) METHODS, SYSTEMS, AND COMPUTER PROGRAM PRODUCTS FOR ANALYZING CARDIOVASCULAR SOUNDS USING EIGEN FUNCTIONS

(75) Inventors: David William Pravica, Greenville, NC (US); Orville W. Day, Jr., Greenville, NC (US); Robert Scott Brock, Greenville, NC (US)

(73) Assignee: East Carolina University, Greenville, NC (US)

( * ) Notice: Subject to any disclaimer, the term of this patent is extended or adjusted under 35 U.S.C. 154(b) by 979 days.

(21) Appl. No.: 11/053,190

(22) Filed: Feb. 8, 2005

(65) Prior Publication Data

US 2005/0234349 A1 Oct. 20, 2005

Related U.S. Application Data

(60) Provisional application No. 60/543,037, filed on Feb. 9, 2004.

(51) Int. Cl.
*A61B 8/06* (2006.01)

(52) U.S. Cl. .................. 600/481; 600/459; 600/407

(58) Field of Classification Search .................. 600/459
See application file for complete search history.

(56) References Cited

U.S. PATENT DOCUMENTS

| | | | | |
|---|---|---|---|---|
| 4,586,514 | A | | 5/1986 | Schlager |
| 4,823,613 | A | * | 4/1989 | Cage et al. ............. 73/861.355 |
| 5,010,889 | A | | 4/1991 | Bredesen et al. |
| 5,012,815 | A | * | 5/1991 | Bennett, Jr. et al. ......... 600/528 |
| 5,311,546 | A | * | 5/1994 | Paik et al. .................... 375/232 |
| 5,515,865 | A | | 5/1996 | Scanlon |
| 5,727,561 | A | | 3/1998 | Owsley |
| 6,048,319 | A | | 4/2000 | Hudgins et al. |
| 6,193,668 | B1 | | 2/2001 | Chassaing et al. |
| 6,278,890 | B1 | * | 8/2001 | Chassaing et al. ............ 600/407 |
| 6,471,655 | B1 | * | 10/2002 | Baura .......................... 600/485 |
| 6,780,159 | B2 | | 8/2004 | Sandler et al. |
| 6,984,922 | B1 | * | 1/2006 | Nagahara et al. ............. 310/334 |
| 2003/0100843 | A1 | * | 5/2003 | Hoffman ..................... 600/538 |
| 2003/0195409 | A1 | * | 10/2003 | Seitz et al. ................... 600/407 |

OTHER PUBLICATIONS

International Search Report for PCT WO 2005/077004; date of mailing Dec. 11, 2006.
Iwata et al. "Algorithm for detecting the first and the second heart sounds by spectral tracking" *Med & Biol. Eng. & Comput.* 18:19-26 (1980).
Shorr et al. "The Prognostic Significance of Asymptomatic Carotid Bruits in the Elderly" *J. Gen. Intern. Med.* 13(2):86-90 (1998).
May et al. "Detection of Hemodynamic Turbulence in Experimental Stenosis: An in vivo Study in the Rat Carotid Artery" *Journal of Vascular Research* 39: 21-29 (2002).

* cited by examiner

*Primary Examiner*—Long V Le
*Assistant Examiner*—Hien Nguyen
(74) *Attorney, Agent, or Firm*—Myers Bigel Sibley & Sajovec

(57) ABSTRACT

Non-invasive methods for detecting arterial disease in vivo include obtaining acoustic signals from a sensor held on an external body region proximate an artery. A complex frequency grid of frequencies and associated lifetimes of the obtained acoustic signals is generated. A predictive model of complex frequencies associated with peak-perturbation acoustic signals attributed to boundary perturbations in vivo that occur with early stage arterial disease is provided. A predictive model of complex frequencies associated with line-perturbation acoustic signals attributed to boundary perturbations in vivo that occur with later stage arterial disease and thickening of arterial junctions is also provided. It is determined whether peak and/or line-perturbation acoustic signals of the predictive models are present to detect whether the subject has arterial disease.

30 Claims, 16 Drawing Sheets xbasis = 70; hbasis = 5; l = 1.;
xlen = 32. l; hlen = 4. l; m = 1.;

xbasis = 70; hbasis = 5; l = 1.;
xlen = 32. l; hlen = 4. l; m = 1.;

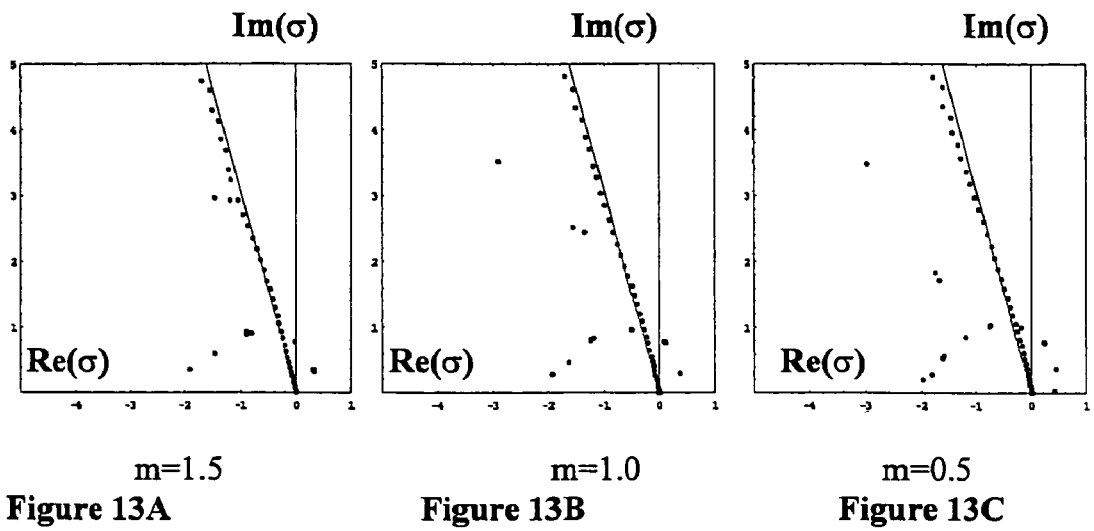
m=1.5
Figure 13A
m=1.0
Figure 13B
m=0.5
Figure 13C
xbasis = 70; hbasis = 5; l = 1.;
$\xi$len=32.; $\eta$len=3.; amp=1.
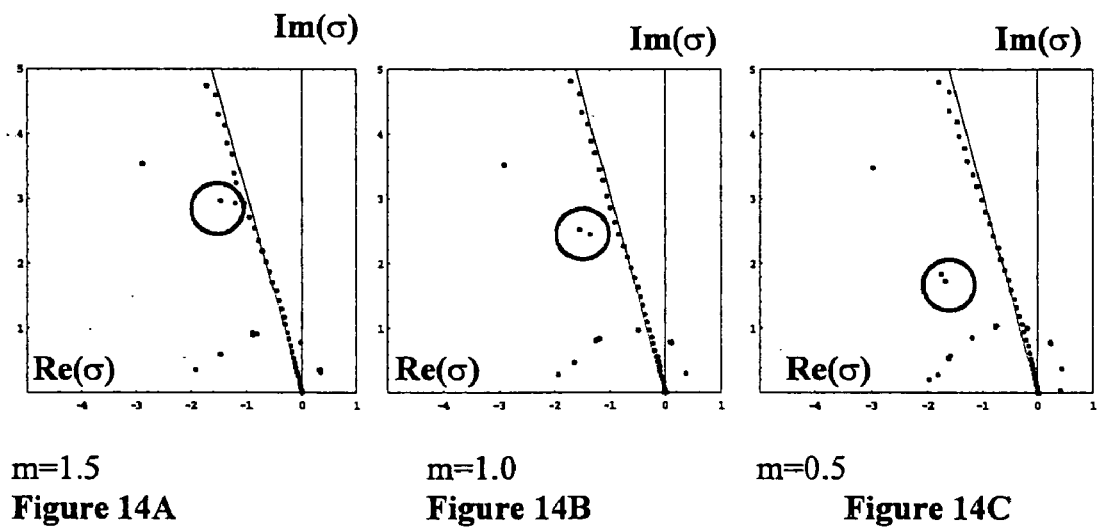
m=1.5
Figure 14A
m=1.0
Figure 14B
m=0.5
Figure 14C
xbasis = 70; hbasis = 5; l = 1.;
$\xi$len=32.; $\eta$len=3.; amp=1.

$\theta = \pi/5.0 , \pi/4.8 , \pi/4.6 , \pi/4.4 ;$

```
xbasis = 70; hbasis = 5; l = 1.;
xlen = 32. l ; hlen = 4. l ; amp = 4.0; m = 1.;
```

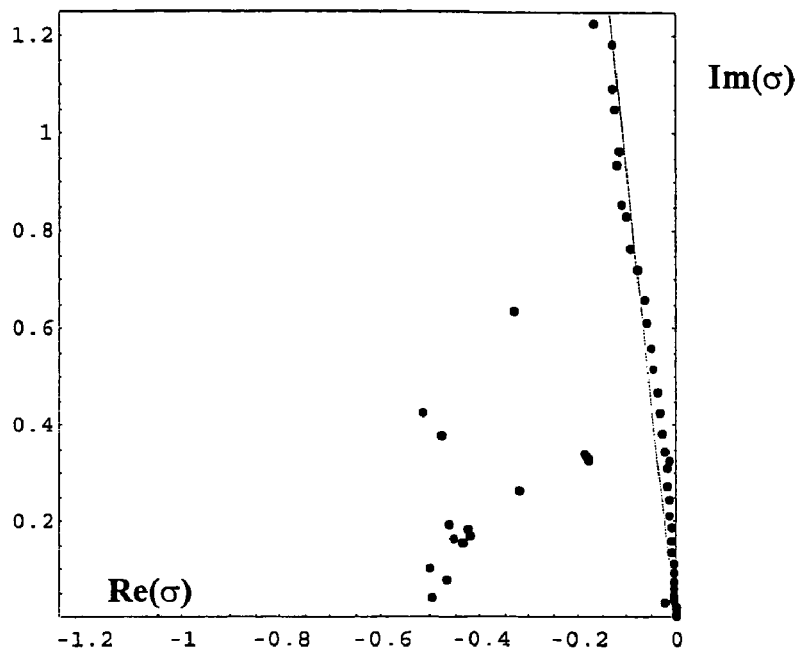
Figure 16A: amp= .5; m = 1.;  θ = π/4.3 ;
xbasis= 70; hbasis= 5; l = 1.; xlen= 32.I ; hlen= 11.I ;
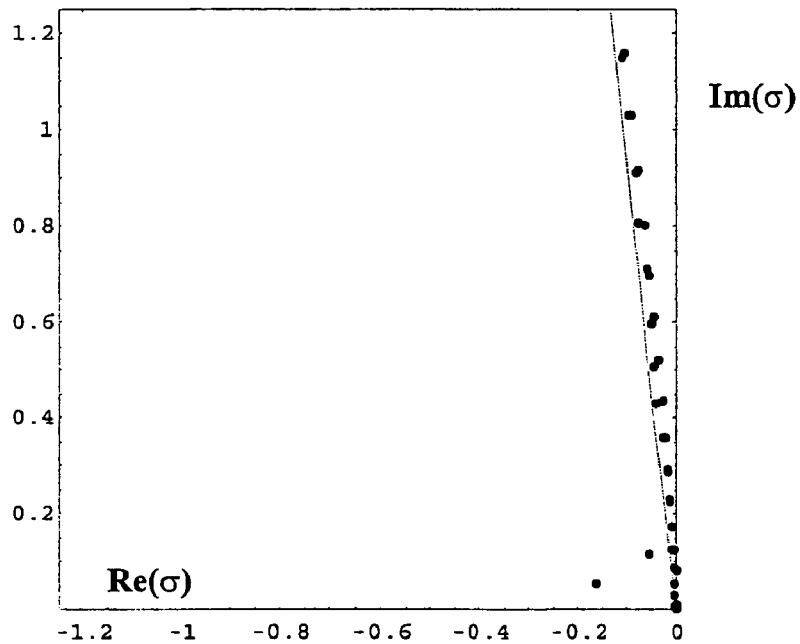
Figure 16B: amp= - .5; m = 1.  θ = π/4.3 ;
xbasis= 70; hbasis= 5; l = 1.; xlen= 32.I ; hlen= 11.I ;

METHODS, SYSTEMS, AND COMPUTER PROGRAM PRODUCTS FOR ANALYZING CARDIOVASCULAR SOUNDS USING EIGEN FUNCTIONS

RELATED APPLICATIONS

This application claims priority to U.S. Provisional Application Ser. No. 60/543,037, filed Feb. 9, 2004, the disclosure of which is hereby incorporated by reference in its entirety.

FIELD OF THE INVENTION

This invention relates generally to the noninvasive detection of cardiac abnormalities, and more specifically to the use of acoustic signals to characterize perturbations in a blood vessel.

BACKGROUND OF THE INVENTION

Health care professionals have observed that certain arteries, such as the carotid arteries from the heart to the brain, can radiate sound waves, called bruits. Bruits can be detected using an examination with a stethoscope, and in severe cases, the bruits can be heard by a health care professional without a stethoscope by pressing their ear against the patient's neck. Early detection of bruits suggests treatment to prevent an embolism, which is a common cause of strokes.

For example, cholesterol, fat and minerals from the blood can be deposited on the inner arterial surface. When these materials build up, they can form plaques, for example, in and around the branching points of the carotid arteries. The branches closest to the heart can form the largest plaques. Plaque can cause great harm if it becomes large enough to pinch off the blood flow, which is referred to as a stenosis in the blood vessel. A plaque can also break off into the bloodstream and can be carried to the brain. Raised plaque may restrict the blood flow through the coronary artery and/or change the surface of the artery from a smooth surface to a rough surface, which can stimulate the formation of a blood clot. Blood clots can slowly build up and narrow the artery and eventually close off the artery to blood flow.

Moreover, the deterioration of arterial health appears related to the elastic properties of the large arteries near the heart. When healthy, these vessels are elastic and can stretch significantly with each pressure wave exerted by the heart. However, myocardial infarction can cause permanent damage to portions of the heart muscle by replacing it with scar tissue that will not contract, which affects the pumping action of the heart.

The detection of bruits resulting from blood vessel abnormalities, such as those discussed above, can be inconsistent. Sometimes a strong sound can be heard when there is little blockage; other times there is no bruit detected even though blockage is sever. Moreover, the human ear may only detect certain frequencies and volumes of sound that may or may not correspond to bruits that indicate a blockage.

SUMMARY OF THE INVENTION

Embodiments of the present invention are directed to non-invasive methods for detecting arterial disease in vivo. Acoustic signals are obtained from a sensor held on an external body region proximate an artery. A complex frequency grid of frequencies and associated lifetimes of the obtained acoustic signals is generated. A predictive model of complex frequencies associated with peak-perturbation acoustic signals attributed to boundary perturbations in vivo that occur with early stage arterial disease is provided. A predictive model of complex frequencies associated with line-perturbation acoustic signals attributed to boundary perturbations in vivo that occur with later stage arterial disease is also provided. It is determined whether peak and/or line-perturbation acoustic signals of the predictive models are present to detect whether the subject has arterial disease.

Further embodiments include a non-invasive system for detecting arterial disease in vivo. An acoustic signal sensor is configured for positioning on an external body region proximate an artery for obtaining acoustic signals. A complex frequency data point generator module is configured to generate a complex frequency grid of frequencies and associated lifetimes using the obtained acoustic signals. A peak-perturbation module in communication with the complex frequency data point generator includes a predictive model of complex frequencies associated with peak-perturbation acoustic signals attributed to boundary perturbations in vivo that occur with early stage arterial disease. A line-perturbation module in communication with the complex frequency data point generator includes a predictive model of complex frequencies associated with line-perturbation acoustic signals attributed to boundary perturbations in vivo that occur with later stage arterial disease. The peak-perturbation module and the line-perturbation module are configured for determining whether peak and/or line-perturbation acoustic signals of the predictive models are present to detect whether the subject has arterial disease.

As will further be appreciated by those of skill in the art, although described above primarily with reference to method aspects, the present invention may be embodied as methods, apparatus/systems and/or computer program products. Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE FIGURES

FIGS. 13A-13C are graphs of resonance frequencies σ as a function of θ for m=1.5, 1.0, and 0.5 units, respectively, according to embodiments of the present invention. The resonance frequencies can be used to measure values such as the reciprocal of variance (m) based on the position of the resonance frequencies.

FIGS. 14C-14C are graphs of resonance frequencies σ as a function of θ for m=1.5, 1.0, and 0.5 units, respectively, according to embodiments of the present invention. Some of the features dependent on variance (1/m) are circled.

FIGS. 16A-16B are graphs of a bump perturbation, i.e. κ>0 (FIG. 16A), and an aneurism perturbation, i.e. κ<0 (FIG. 16B), derived at using a numerical simulation of complex-scaling methods according to embodiments of the present invention.

DETAILED DESCRIPTION OF EMBODIMENTS OF THE INVENTION

Figure 1:
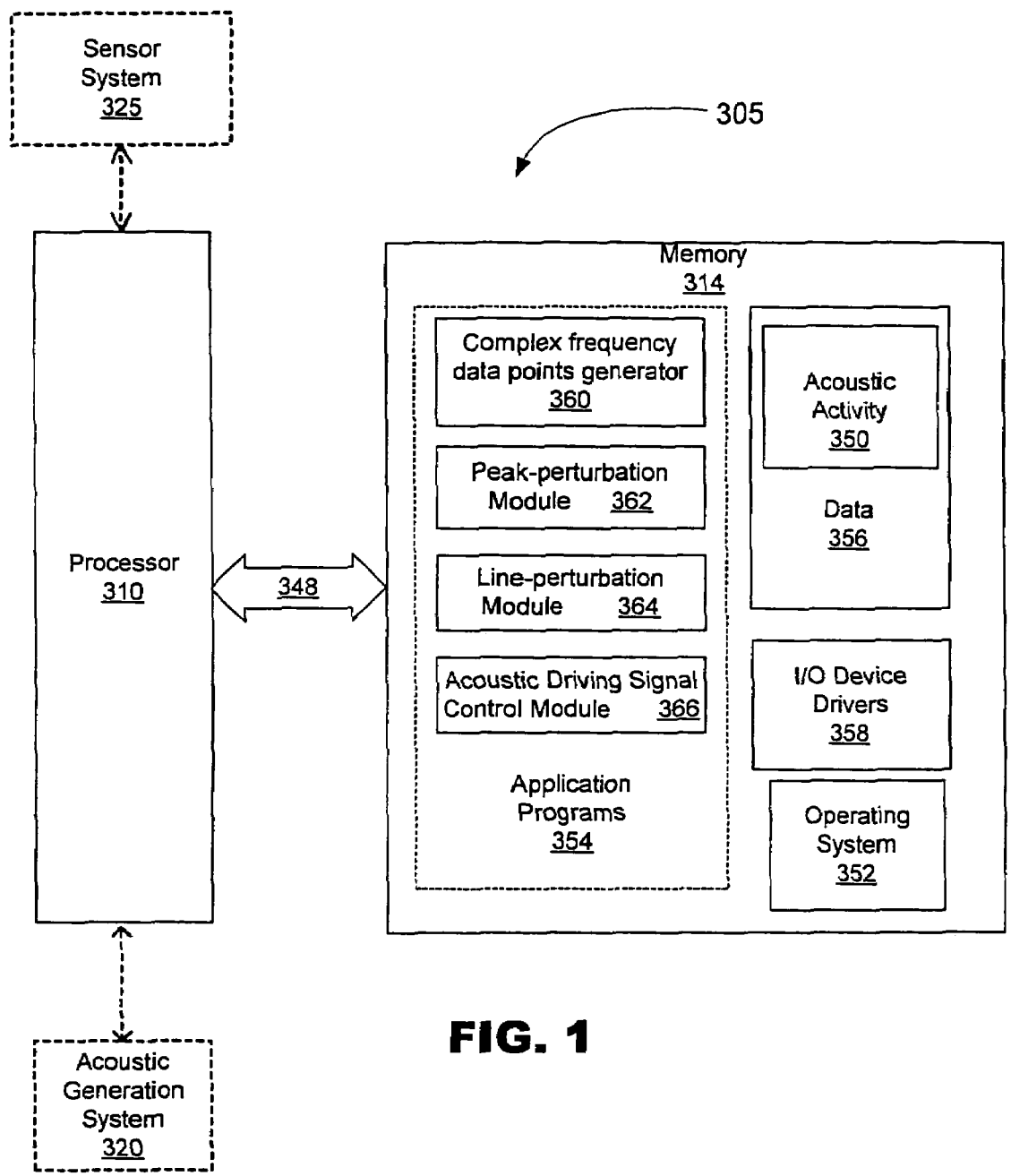
FIG. 1 is a schematic diagram of systems and computer program products according to embodiments of the present invention.

The present invention will now be described more particularly hereinafter with reference to the accompanying drawings, in which preferred embodiments of the invention are shown. The invention, however, may be embodied in many different forms and is not limited to the embodiments set forth herein; rather, these embodiments are provided so that the disclosure will fully convey the scope of the invention to those skilled in the art. Like numbers refer to like components throughout.

According to embodiments of the present invention, discrete frequencies and corresponding frequency lifetimes from an acoustic signal detected from an artery can be used to characterize fluid flow through a blood vessel. A predictive model of complex frequencies associated with various boundary perturbations that occur with arterial disease is provided. A sensor held on a subject's neck proximate the carotid artery obtains acoustic signals from the artery. A complex frequency grid of frequencies and associated lifetimes of the obtained acoustic signals can be generated. The acoustic signals are analyzed to determine whether perturbations of the predictive model are present, and henceforth to conclude whether or not the subject has arterial disease to a level deemed important. Types of boundary perturbations and responses include the following examples:

Peak-perturbation Case: A peak-perturbation on a smooth surface, such as an arterial wall, is a circularly shaped (or nearly so) protrusion from the surface culminating in a peak, like a mountain-peak. Uniform flow parallel to the surface moves around the peak, resulting in a side-to-side displacement of the fluid. The resulting behavior of the fluid can include the formation of a von Karman vortex street, at least for low to moderate Reynolds numbers, for example Re=40 to 1000 (M. Griebel, T. Dornseifer, T. Neunhoeffer, *Numerical Simulation in Fluid Dynamics: A Practical Introduction*, SIAM Monographs, Philadelphia Pa., 1997). For systems in which Re<40, oscillations may not be created by the system. For systems in which Re>1000, there may be so many oscillations that the signal can appear noisy and resonances may be difficult to detect. Embodiments of the present invention can be used to predict signals produced by a single isolated boundary peak-perturbation. Single peak-perturbations generally correspond to the beginning of disease when particles first enter the wall of an artery and create a small bump. The corresponding waves typically move side-to-side and stay near the wall. The side-to-side sheering stress may cause the artery walls to oscillate and can create a detectable sound wave.

Line-perturbation Case: A line-perturbation on a smooth surface, such as an arterial wall, is a linearly shaped (or nearly linearly shaped) protrusion from the arterial surface. A linear bump may form because several nearby peak-perturbations have joined, or because an arterial junction joining one to two tubular pathways has stiffened and/or collected deposits. Side-to-side motion of the fluid can be hindered, but up-down motion (i.e., toward and away from the wall) may be expected. Line-perturbations may be similar to lee waves that appear on the lee side of mountain chains as air masses pass over them (J. R. Holton, *An Introduction to Dynamic Meteorology*, Academic Press 1979). Embodiments of methods according to the present invention can be used to predict signals that can be produced produced by a large boundary perturbation that has spread or a line-perturbation. Line-perturbations may correspond to the later stages of arterial disease on the walls, or any stage of disease for arterial junctions. The corresponding waves can move toward and away from the wall. The up-and-down forces may also cause the artery walls to oscillate, but the detected sound waves may have different frequencies than in case of peak-perturbations.

It should be understood that some geometries that may be more elaborate can lead to hairpin vorticies (as described in Balaras et. al. in the 2003 Summer Bioengineering Conference, June 2003, Florida, pp. 413-414) and can be detected as combinations of peaks and/or line-perturbations.

More specifically, the predictive model can include 1) a predictive model of complex frequencies associated with peak-perturbation acoustic signals attributed to boundary perturbations in vivo that occur with early stage arterial disease, and 2) a predictive model of complex frequencies associated with line-perturbation acoustic signals attributed to boundary perturbations in vivo that occur with later stage arterial disease and/or along arterial junctions. The obtained acoustic signals from the sensor proximate the carotid artery can be analyzed to determine whether the characteristic peak and/or line-perturbation signals of the predictive models are present to detect whether the subject has arterial disease. In some embodiments, a driving acoustic signal can be applied to the subject, such as proximate the subject's heart, to modify the acoustic signals obtained in the carotid artery. Alternatively, in some embodiments, sensors can be placed on both sides of the neck, on the heart and on the lower abdomen simultaneously. The sensors may be connected by a single device, such as a jacket or cuff other wearable device configured to hold the sensors in position at various places in the body. In one particular example, thirteen sensors are positioned on the following arterial locations: two sensors at the carotid artery at the common/external/internal locations (anterior neck), two sensors at the basilar/vertebral artery (posterior neck), two sensors at the abdominal aorta/iliac artery (abdomen), two sensors at the renal artery (middle back), two sensors at the femoral artery (legs), two sensors at the brachial artery (arms), and one sensor at the heart. Systems, methods and computer program products for detecting arterial disease in vivo are provided. Sound waves in the body may be detected, for example, using standard piezo-electric technology, such as is employed in a SIDS detector, e.g., U.S. Pat. No. 5,515,865.

FIG. 1 is a block diagram of exemplary embodiments of data processing systems that illustrates systems, methods, and computer program products in accordance with embodiments of the present invention. The data processing system 305 includes a processor 310 that can send and receive information to or from a sensing system 325 and/or an acoustic signal generation system 320. The data processing system 305, acoustic signal generation system 320 and/or the sensing system 325 may be implemented externally from the patient. The data processing system 305, acoustic signal generation system 320 and/or the sensing system 325 can be provided as separate components or two or more systems or system components can be provided as an integrated system. As illustrated, the processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM. The memory 314 may include several categories of software and data used in the data processing system 305: an operating system 352; application programs 354; input/output (I/O) device drivers 358, and data 356.

As will be appreciated by those of skill in the art, the operating system 352 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, or proprietary operating systems. The I/O device drivers 358 typically include software routines accessed through the operating system 352 by the application programs 354 to communicate with devices such as I/O data port(s), data storage 356 and certain components of memory 314 components and/or the shock generation system 320, sensing system 325 and/or drug delivery system 340. The application programs 354 are illustrative of the programs that implement the various features of the data processing system 305 and preferably include at least one application which supports operations according to embodiments of the present invention. Finally, the data 356 represents the static and dynamic data used by the application programs 354, the operating system 352, the I/O device drivers 358, and other software programs that may reside in the memory 314. The data 356 may include acoustic activity data 350, such as acoustic signals sensed from the sensor system 325 and/or a record of acoustic signals generated by the acoustic generation system 320. The sensor system 325 can include a sensor array that can be positioned proximate the carotid arteries in a subject. For example, the sensor array can be configured to detect acoustic signals around a portion of the subject's neck, around the entire circumference of the subject's neck or around the chest or abdomen or temples or other external body parts.

As shown in FIG. 1, the application programs 354 can include a complex frequency data point generator 360, a peak-perturbation module 362, a line-perturbation module 364, and/or an acoustic driving signal control module 366. The complex frequency data point generator 360 can generate data points in the complex frequency grid. These data points can be used by the peak-perturbation module 362 and the line-perturbation module 364 to determine if the data points indicate the presence of a peak-perturbation or line-perturbation, respectively. The complex frequency data point generator 360 can generate a complex frequency grid of frequencies and associated lifetimes of the obtained acoustic signals in the acoustic activity data 350, for example, using standard techniques such as Fourier transforms and Burg adaptive analysis. Examples of complex frequency data points generated in a complex frequency grid are given in Examples 1 and 2.

The peak-perturbation module 362 can include a predictive model of complex frequencies associated with peak-perturbation acoustic signals attributed to boundary perturbations in vivo that occur with early stage arterial disease. A peak-perturbation can be a signal produced by single isolated boundary perturbations. This generally corresponds to the beginning stages of arterial disease when particles, such as plaque, first enter the wall of an artery and create a small bump. When blood flows through the channel, and around a peak perturbation, fluid waves are generated that move generally side-to-side parallel to the arterial wall and are generally localized proximate the arterial wall. This side-to-side shear stress can cause the arterial walls to oscillate and create a detectable sound wave. Thus, complex frequencies that are isolated complex frequencies of low frequency may indicate the presence of peak-perturbations associated with early stage arterial disease. Examples of low, isolated complex frequencies that may indicate the presence of peak-perturbations and related calculations are discussed in Examples 1 and 3.

The line-perturbation module 364 can include a predictive model of complex frequencies associated with line-perturbation acoustic signals attributed to boundary perturbations in vivo that occur with later stage arterial disease and disease at junctions of splitting of vessels that can form a line shape within the flow channel. The junction is also known as a flow-divider. Relatively large protrusions of particles, such as plaque, that substantially obstruct blood flow may indicate later stages of arterial disease. When blood flows through a blood vessel having such obstructed flow, waves are produced that move toward and away from the arterial wall, resulting in tensile compressive forces on the arterial wall. For the flow-divider, hardening and plaque buildup can occur along the arterial-junction line, and when this occurs the fluid flow can exhibit line-perturbation characteristics. The oscillations of the arterial walls may generate acoustic signals which, when a complex frequency scatter-plot is generated, lie substantially on ellipses such that each ellipse includes several frequencies. Thus, complex frequencies that lie substantially in ellipses with a plurality of frequencies on each ellipse may indicate the presence of line-perturbations. Examples of line-perturbation frequencies and related calculations are discussed in Examples 2 and 3.

As described above, the complex frequency data point generator 360 can generate a frequency scatter-plot of the acoustic activity data 350 in the complex frequency grid. The peak-perturbation module 362 can determine if low, isolated complex frequencies indicative of peak-perturbations indicating early stage arterial disease are present. The line-perturbation module 364 can determine if complex frequencies that lie substantially in an ellipse indicating later stage arterial disease. Thus, a determination of whether the subject has arterial disease can be made. Embodiments of the present invention may also be used during a surgery, for example, but not restricted to, a minimally invasive surgery, to monitor the shape of the arteries using sound. Such information may be useful in the reconstruction of arterial pathways so as to allow less obstructed blood flow. Methods according to the present invention can also be used to develop a correlation between received signals and the shape of the channel pathways.

In some embodiments, the acoustic driving signal control module 366 can control the acoustic signal generation system 320 to provide an acoustic driving signal to the subject. For example, the acoustic signal generation system 320 can include a low frequency generator that can apply a low frequency acoustic signal proximate the heart of the subject. The low frequency acoustic signal can be between about 1 Hz to about 20 Hz. The acoustic signal generation system 320 can control and vary the frequency of the acoustic signal generated thereby. As discussed above, the sensor system 325 detects acoustic signals using a sensor positioned proximate the carotid artery of the subject. Thus, various driving signals and their respective sensed signals can be recorded. A correlation between the driving signals and the respective sensed signals can be determined, and the extent of the atherosclerotic disease can be determined using a predictive model. For example, a low frequency driving signal can be applied externally to a patient's lower rib cage, i.e., to the lower heart chamber. If low frequency acoustic signals are produced by perturbations in the artery, the addition of the low frequency acoustic signal can cause a "beat" in the detected signal in the neck region. One or more of the application programs 354 can provide a phase-lock loop to enhance the received signals according to techniques known to those of skill in the art.

In some embodiments, a tracking range can be determined, for example, using the mathematical results discussed in Examples 1-3 to determine an approximation of the vibration signals that can be used in locking in the phase of a signal. For example, once a tracking range is established, the acoustic driving signal control module 366 can control the acoustic signal generation system 320 to adjust an acoustic driving signal generated within the tracking range. The acoustic driving signal control module 366 can tune the driving signal within the tracking range to determine constructive and/or destructive interference points between the driving signal and the acoustic signals due to bruits in the arteries. The constructive interference points generally occur at frequencies where a portion of the signal from the bruits and driving signal are approximately equal. In this manner, resonance frequencies in the acoustic signals produced by the perturbations in the arteries due to aneurisms and/or plaque deformities and/or other cardiovascular diseases can be determined.

In some embodiments, the data processing system 305 can be used to calibrate the calculations with respect to a patient's heart chamber and/or the size and shape of the patient's carotid arteries. For example, viewing the carotid arterial system, from heart to head, as a closed chamber whose walls stretch through the blood-pressure cycle, the input waves can either constructively or destructively interfere with the eigenmodes of the chamber. Basic information on the size and shape of the chamber from the detected signals can be obtained, e.g., using techniques known to those of skill in the art. (M. Reed and B. Simon, *Analysis of Operators*, Academic Press, Inc., London 1978).

Although the present invention is illustrated, for example, with reference to the complex frequency data point generator 360, the peak-perturbation module 362, the line-perturbation module 364, and the acoustic driving signal control module 366 being an application program 354 in FIG. 1, as will be appreciated by those of skill in the art, other configurations may also be utilized that still benefit from the teachings of the present invention. For example, the complex frequency data point generator 360, the peak-perturbation module 362, the line-perturbation module 364, and/or the acoustic driving signal control module 366 may also be incorporated into the operating system 352, the I/O device drivers 358 or other such logical division of the data processing system 305. Thus, the present invention should not be construed as limited to the configuration of FIG. 1, which is intended to encompass any configuration capable of carrying out the operations described herein.

The I/O data port can be used to transfer information between the data processing system 305 and the acoustic signal generation system 320, sensing system 325, or another computer system or a network (e.g., the Internet) or to other devices controlled by the processor. These components may be conventional components such as those used in many conventional data processing systems that may be configured in accordance with the present invention to operate as described herein.

Figure 2:
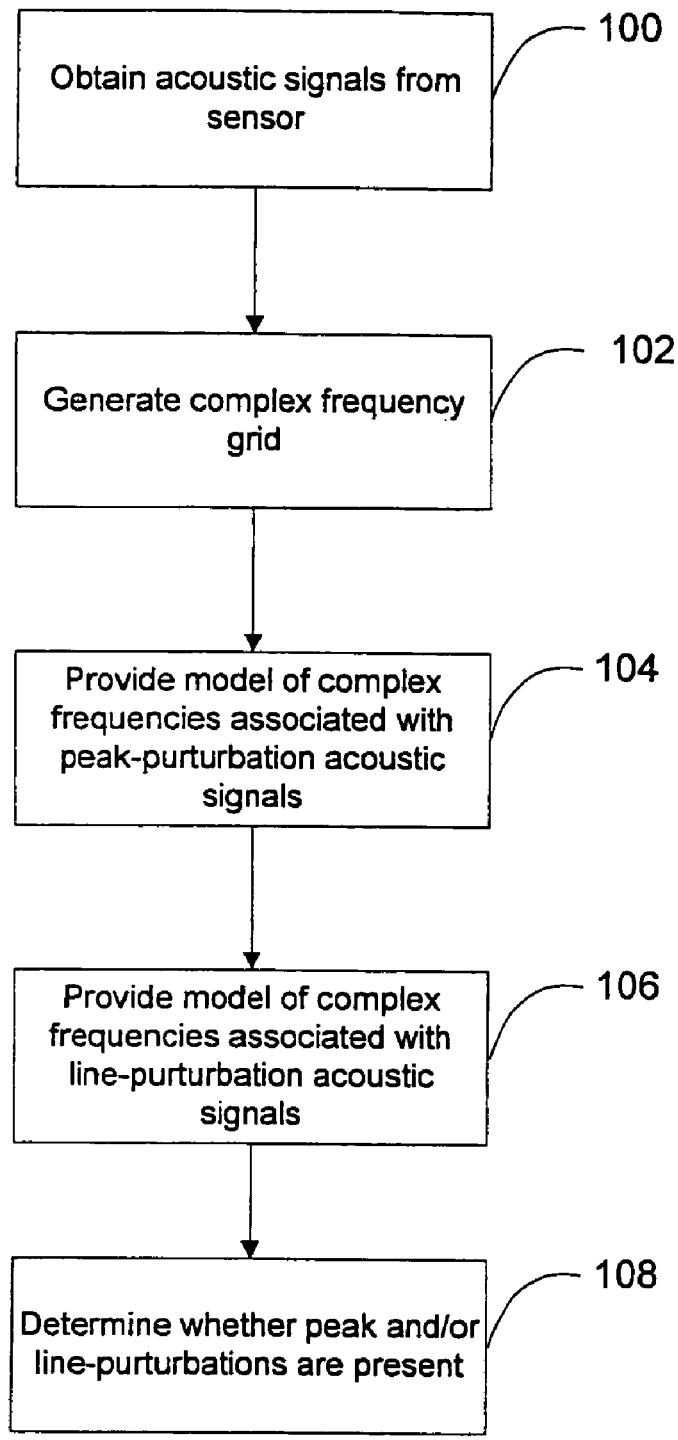
FIG. 2 is a flow chart of operations according to embodiments of the present invention.

Non-invasive methods of detecting arterial disease in vivo according to embodiments of the invention that can be carried out by the systems shown in FIG. 1 are illustrated in FIG. 2. Acoustic signals are obtained from a sensor held on a subject's neck proximate a carotid artery (Block 100). A complex frequency grid of frequencies and associated lifetimes of the obtained acoustic signals is generated (Block 102). Examples of complex frequency grids are discussed in Examples 1 and 2 below.

A model of complex frequencies associated with peak-perturbation acoustic signals is provided (Block 104). Peak-perturbation acoustic signals can be isolated complex frequencies of low frequency. Examples of peak-perturbation acoustic signal models are discussed in Example 1. As discussed in Example 1, the predictive model of peak-perturbation acoustic signals can include eigenfunctions corresponding to characteristic peak-perturbations of flow through the carotid artery.

A model of complex frequencies associated with line-perturbation acoustic signals is also provided (Block 106). Line-perturbation acoustic signals can be frequencies that lie substantially in ellipses with a plurality of frequencies on each ellipse. Examples of line-perturbation acoustic signals are discussed in Example 2. As discussed in Example 2, the predictive model of line-perturbation acoustic signals can include eigenfunctions corresponding to characteristic line-perturbations of flow through the carotid artery.

The obtained acoustic signals from the sensor can be analyzed to determine whether peak- and/or line-perturbations are present (Block 108). In particular, a pattern of resonance frequencies can be identified, such as by determining the ratios of the resonance frequencies and values of the strongest signals. Peak-perturbation acoustic signals, for example, result in a pattern of isolated complex frequencies of ultra low frequency (ULF), for example between about 10 Hz or lower and 300 Hz. (Example 1). The low frequencies may include inaudible and audible frequencies. If the background flow speed is $U_0$ (typically less than about 50 cm/sec) in a blood vessel of width h (typically less than about 2 cm) for blood having a kinematic viscosity $v_0$, (typically between about 0.05 to 0.20 Stokes (Stokes=cm²/sec)) for a simple peak boundary (Example 1) perturbation with mean curvature κ the main peak frequency can be expressed as $$f \sim 0.212 \kappa U_0 - 5.35 v_0 \kappa^2$$

which generally has a lower limit on size detection of peak perturbations of about 0.1 mm.

For typical blood flow and perturbation sizes, oscillations can range between about 10 and 300 Hz, corresponding to ULF waves. In some embodiments, the ULF waves can be as low as about 0.1 Hz. Line-perturbation acoustic signals result in a discrete family of complex frequencies that substantially lie on an ellipse with a plurality of frequencies on each ellipse (Example 2). A pattern of line-perturbation resonance frequencies for uniform flow $U_0$ in a blood vessel of width h, for blood having a kinematic viscosity $v_0$ for a simple boundary perturbation with peak curvature κ, can be identified by identifying a family of complex frequencies having the formula:

$$f_n = \lambda_0 v_0 \exp[i\beta_n]$$

where the frequency radius is: $\lambda_0 = (U_0/2v_0)^2 \exp[-2(h\ \kappa)/3]$ and the angles are: $\beta_n = 2 \arccos[(v_0(h\kappa)^{1/2}/U_0 h)(2n+1)]$ for n=0, 1, 2, ... M. In some embodiments, M is an integer that is less than or equal to twenty. For typical blood flow and perturbation size, waves will range between about 0.01 to about 300 Hz, corresponding to low ULF waves.

As discussed in Example 1 and Example 2 the eigenfunctions can be determined by applying complex scaling to a conformal transformation of the Navier-Stokes equation. The identified resonance frequencies and/or the identification of peak and/or line-perturbation acoustic signals can be used to detect whether the subject has arterial disease. In some embodiments, the blood vessel can be characterized according to the eigenvalues of the identified eigenfunctions. For example, an occlusion in the blood vessel can be identified, as well as the size, location, rigidity and shape of the occlusion. Blood has an approximate kinematic viscosity of $v_0 \sim 0.05$-$0.20$ cm²/sec, and flow rate $U_0 \sim 0$-$50$ cm/sec. Thus, for peak perturbations, peak curvature may be directly related to frequency as follows:

$$\kappa \sim [0.212 U_0 - (0.045 U_0^2 - 21.4 v_0 f)^{1/2}]/[10.7 v_0]$$

Large curvature κ may correspond to a small peak, and small κ may correspond to a larger and more spread-out perturbation, that is, a perturbation having a higher height and larger width. Decreasing κ may imply a worsening condition.

For line perturbations, where h denotes the width of the blood vessel generating a sound wave, the relationship can be expressed as follows:

$$h\kappa \sim (3/2) \ln [U_0^2/(4 v_0 |f_n|)]$$

Figure 10:
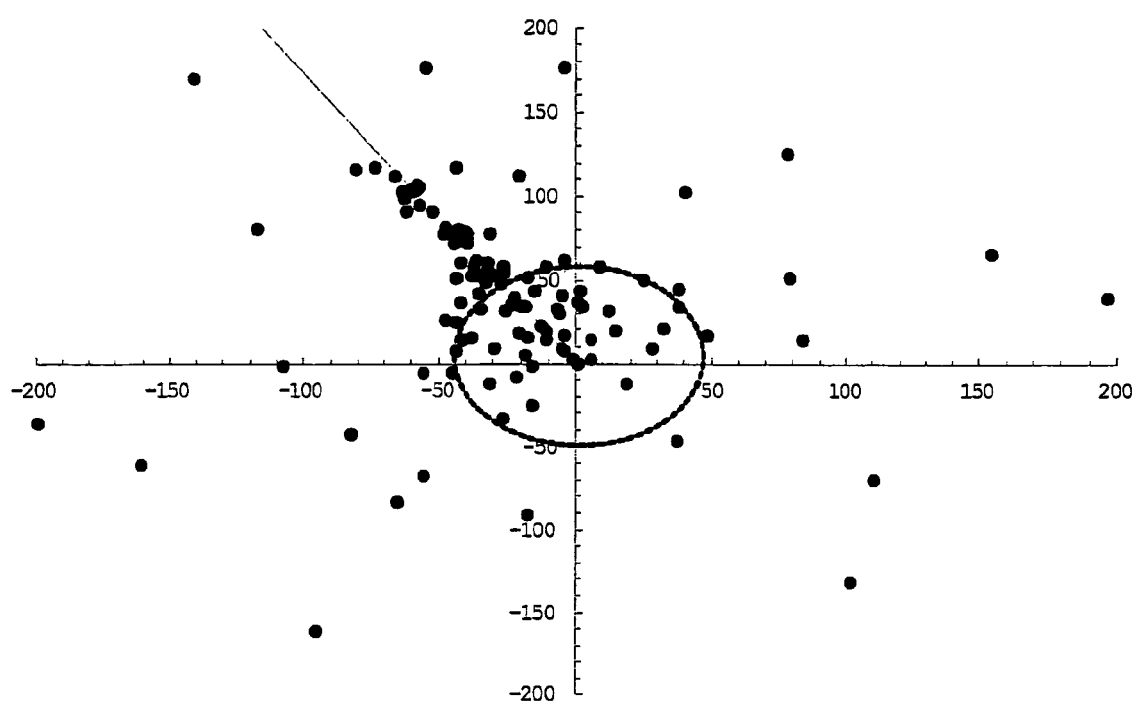
FIG. 10 is a graph of the resonances from the numerical procedure for a Reynold's number of 50, with an angle of π/6 for boundary stenosis according to embodiments of the present invention.
Figure 18:
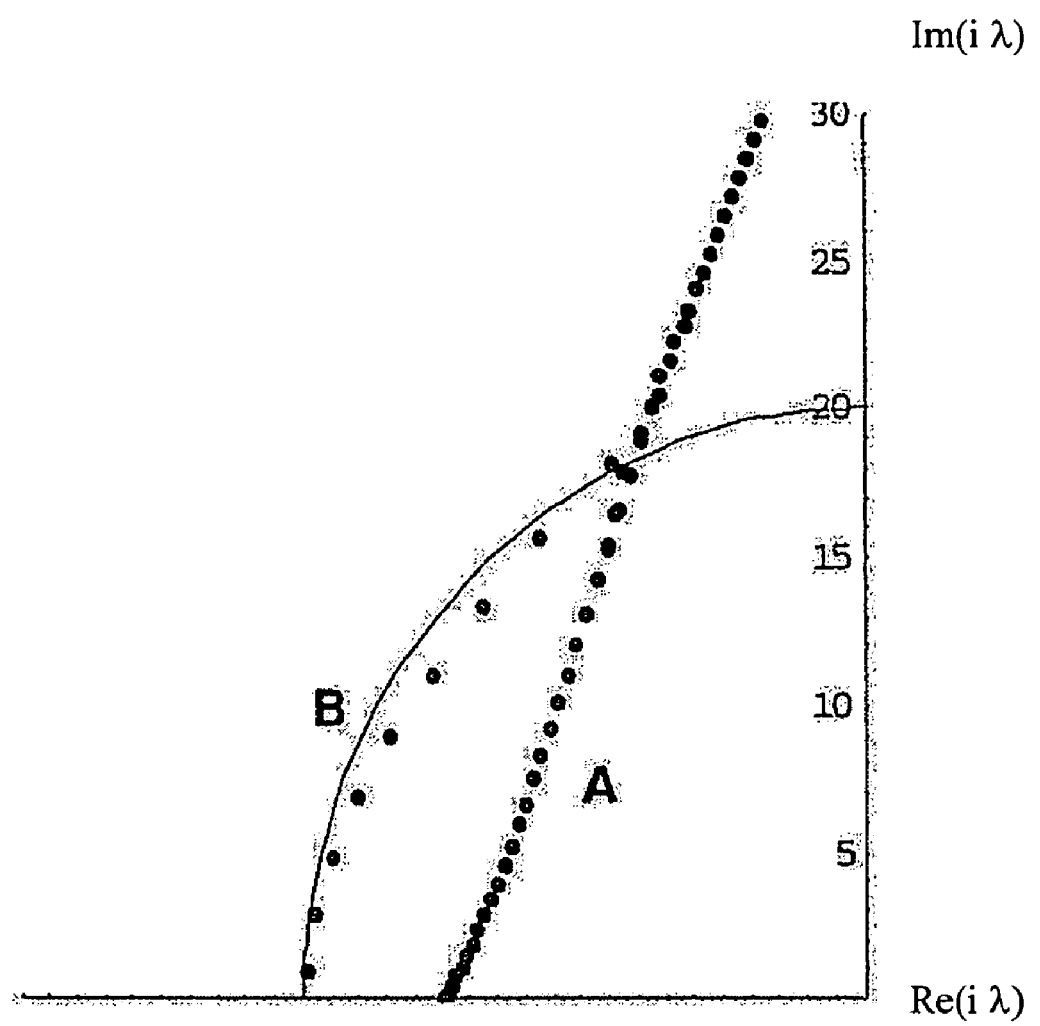
FIG. 18 is a graph of the output from a computer program that uses the method of complex scaling as applied to flow through the channel configuration shown in FIG. 8. The line of dots labeled "A" correspond to continuous frequencies, which are not expected to be observed. The sequence of dots, near the inscribed arc and labeled "B," are the resonances, also referred to as complex frequencies.

Using this relationship, hκ generally corresponds to the amount of blockage in an artery. Here the frequencies show up in the form of ellipses that may be somewhat distorted with many frequencies residing along an ellipse when plotted in the complex plane. Initial results are shown in FIG. 10 and improved results appear in FIG. 18. Higher frequencies for line perturbations may correspond to greater blockage, and poorer health. More detailed information may also be available in the equations obtained, since, for example, $\beta_n$ actually has a sequence or family of states, or extra harmonics, associated with this lowest frequency value. This is further discussed in Example 2 where the family $\beta_{l...n}$ is defined.

Similarly, an aneurism can be identified and/or characterized based on the complex frequencies. The frequencies are much fainter in this case and come from theoretical and numerical studies. For example, the above equations can be used to identify aneurisms by assuming a negative value for κ or "amp", for example, as discussed in Example 4.

EXAMPLE 1

A Quantum Mechanical Approach to the Modeling of Laminar Fluid Flow past a Circular Cylinder Peak-perturbation Model The following example provides a method for theoretically predicting signals produced by single isolated boundary perturbations. Single isolated boundary perturbations may correspond to the beginning of coronary disease when particles first enter the wall of an artery and create a small bump. The corresponding waves generally move side-to-side and are localized near the arterial wall. The side-to-side sheering stresses may cause the arterial wall to oscillate at substantially the same frequency, thus producing a sound wave, which may be detected, for example, by standard piezo-electric technology.

Accordingly, the classical problem of uniform incompressible fluid flow past a circular cylinder of cross-sectional radius $r=r_0$ can be applied. The Joukowski transformation $\zeta = z/r_0 + r_0/z$ converts an irrotational flow pattern into a simple steady flow over a flat strip of fixed width. A boundary condition is chosen that allows slip. The Navier-Stokes equation may be re-expressed in the vorticity-stream function formulation. This can provide a non-symmetric Schrödinger equation where the Reynolds number Re becomes the coupling parameter for a transformed potential and for a first order term. Numerical complex scaling may be used to find the complex frequencies of the system. Comparison may be made with a series of numerical solutions for Re numbers ≦2000 where it is known that there are two types of phenomena: 1) the appearance of down-stream vortices in the wake region near the boundary (which correspond with growing bound states), and 2) fluid oscillations (which correspond with top resonances). Many properties can be extrapolated from the low Reynolds numbers, where the phenomena, initially, is manifested, to larger Reynolds numbers.

I. Introduction

The classical problem of uniform incompressible fluid flow past a rigid cylinder and the phenomena of its flow pattern can be addressed using a quantum mechanical approach. The Joukowski transformation $\zeta = z/r_0 + r_0/z$ applied to the cross-section of the circular cylinder of radius $r=r_0$ (See C. Pozrikidis, *Introduction to Theoretical and Computational Fluid Dynamics*, Oxford: Oxford University Press, 1997) conformally transforms into a flat strip: and the irrotational flow becomes a uniform stream. The consequence of using a conformal transformation is the introduction of analytic terms and factors into the Navier-Stokes equations that can be related to boundary geometry. These analytic terms and factors may be significant inside the flow region, the boundary of which may be simplified, as discussed herein. The resulting fluid equations can be studied as a Schrödinger equation, which has bound and quasi-bound (or resonance) states. This approach allows a discussion of a downstream inverse scattering problem where observing the degrees of freedom within a downstream flow profile implies certain parameters of the upstream boundary conditions, such as wall thickness, size and number of peaks and lines, hardness of peak and line perturbations, etc. For example, the basic formula used is, $$f = St\, U_0/(2r_0)$$

where f is the received frequency, $U_0$ the uniform flow speed, St the Strouhal number for the peak perturbation in a uniform flow, and $r_0$ the radius of the peak perturbation. Then the radius of the peak $r_0$ is determined from, $$r_0 = St\, U_0/(2f)$$

which is one indicator of arterial health. If many frequencies of nearly the same value are heard, then many peaks can be inferred. If the frequency f varies with the flow speed $U_0$, then the peak parameter's radius and shape may also be changing, which could imply a softer peak perturbation. Soft perturbations may be associated with more risk to the incidence of stroke because they can break off and enter the blood stream more easily than hard perturbations. Finally, subtle variations in the frequency can indicate the extent to which the flow channel, vis-à-vis the artery, stretches during a cardiac pulse cycle.

The problem of flow past a sphere has many applications in engineering, meteorology and medicine. In the case of blood flow, different types of waves are produced by perturbations of the arterial walls (see C. G. Caro, T. J. Pedley, R. C. Schroter, W. A. Seed, The Mechanics of the Circulation, Oxford: Oxford University Press, 1978). As discussed above, in some cases of stenosis in the carotid arteries, bruits can be heard emanating from the neck (see C. G. Caro, T. J. Pedley, R. C. Schroter, W. A. Seed, *The Mechanics of the Circulation*, Oxford: Oxford University Press, 1978 chaps. 5 and 12). For viscous flows, a low frequency wave phenomena can be derived by assuming small oscillations and solving the resulting linearized heat equation, while satisfying appropriate boundary conditions (L. D. Landau, E. M Lifshitz, Fluid Mechanics, Oxford: Pergamon Press Ltd., 1959). These first-order waves are known as the von Kármán vortex street. Unfortunately, even for simple boundaries, this may be quite difficult to do theoretically. Resorting to finite element methods may result in a loss of the physical understanding behind the mechanism generating the vortex street. Embodiments of the present invention may provide improved calculations of complex frequencies characteristic in various flow problems.

For Re>4, fluid separation may be observed behind the cylinder (see M. Griebel, T. Dornseifer, T. Neunhoeffer, *Numerical Simulation in Fluid Dynamics: A Practical Introduction*, SIAM Monographs, Philadelphia Pa., 1997). As the Reynolds number is increased above 40, vortex shedding can occur and waves (e.g., vortex street) may appear as an oscillation with amplitude perpendicular to the direction of fluid flow. The frequency f of oscillations for the case of a cylinder is given by the Strouhal relation in a flow of average speed $U_0$ past a cylinder of radius $r_0$ (from M. Griebel, T. Dornseifer, T. Neunhoeffer, *Numerical Simulation in Fluid Dynamics: A Practical Introduction*, SIAM Monographs, Philadelphia Pa., 1997), $$f = St(Re)U_0/(2r_0),\ St(Re) \sim 0.212 - 5.35/Re, \qquad (1.0)$$

valid for 40<Re<2000.

The methodology in Example 1 is not numerical, although matrix elements are obtained by a computational approximation (see B. Mohammadi, O. Pironneau, *Analysis of the K-epsilon Turbulence Model*, John Wiley & Sons, Chichester England, 1994, for a discussion of some difficulties with finite element convergence for this problem). Extreme values of the vorticity oscillations in the flowing fluid are of interest.

The vorticity $\omega$ (t, x, y) and the stream function $\psi$(t, x, y) may be treated as state variables for the fluid-flow system. Modeling the generation of vorticity by this method is described in K. E. Gustarson, J. A. Sethian, *Vortex Methods and Vortex Motion*, SIAM, Philadelphia Pa., 1991. In the present Example 1, it is suggested that vorticity can be created by a potential function concentrated near a bounding wall. The potential function leads to a large family of unstable oscillating states, or resonances. Although the focus here is only on a few low frequency states, the number of resonances may grow with Re and can be one source for the onset of turbulence. Strong non-linear effects, as arise in Lighthill's equation (see e.g. Goldstein, "Aeroacoustics", 1976 McGraw-Hill), are not considered in Example 1, although their significance to turbulence in the flow region may increase with Re.

The first result corresponds with a downstream fluid-separation vortex in the wake of the cylinder, which appears for Re>0 that is sufficiently large. For example, "sufficiently large" Re can be between about 4 to about 10. Excluding differential vorticity advection (as defined in J. R. Holton, *An Introduction to Dynamic Meteorology*, Academic Press 1979), the vortex actually increases exponentially in size over time. The second main result is the existence of top resonances in a two-dimensional flow concentrated in the upstream portion of the cylinder boundary. In particular, $St(Re) \simeq 0.212$ as stated in M. Griebel, T. Dornseifer, T. Neunhoeffer, *Numerical Simulation in Fluid Dynamics: A Practical Introduction*, SIAM Monographs, Philadelphia Pa., 1997 and K. E. Gustarson, J. A. Sethian, *Vortex Methods and Vortex Motion*, SIAM, Philadelphia Pa., 1991. Due to this observation, one can conclude that ". . . the frequency of vortex shedding from a given body, and hence the pitch of the sound produced, increases in proportion with the flow velocity." See pp. 75, C. G. Caro, T. J. Pedley, R. C. Schroter, W. A. Seed, *The Mechanics of the Circulation*, Oxford: Oxford University Press, 1978.

Example 1 is organized as follows. In section 2, the fluid equations are discussed along with the simplifying assumptions. In section 3, uniform flow past a cylinder is considered. In section 4, top resonances are studied for the corresponding Schrödinger equation and complex scaling is employed. A connection can be established between the fluid flow equations around compact objects and an appropriate Schrödinger equation that has complex eigenvalues. In sections, it can be shown that the lowest frequencies can contain information on the shape parameters of the perturbation.

2. Fluid Equations and Assumptions

The two-dimensional Navier-Stokes equations in variables $(x, y) \in R^2$ for incompressible fluid flow are, $$\partial_t \vec{q} + \vec{q} \cdot \vec{\nabla} \vec{q} = -\rho_0^{-1} \vec{\nabla} p + \nu_0 \nabla^2 \vec{q}, \qquad (2.1a)$$

$$\vec{\nabla} \cdot \vec{q} = 0, \qquad (2.1b)$$

where the kinematic viscosity $\nu_0$ and the density $\rho_0$ are constant. The operator, $$\vec{q} \cdot \vec{\nabla} \equiv q_1 \partial_x + q_2 \partial_y + q_3 \partial_z, \qquad (2.1c)$$

is associated with advection. The dependent variables are $\vec{q}$, the velocity field, and p, the pressure. In two-dimensions, the divergence equation $\vec{\nabla} \cdot \vec{q} = 0$ implies the existence of a stream function $\psi(t,x,y)$ which gives $\vec{q} = \text{curl}(-\psi \hat{k})$. Elimination of the pressure by taking the curl of (2.1a) leads to an equation for the vorticity ($\omega = \nabla^2 \psi$, also written $\omega = \Delta\psi$. The evolution of the state ($\psi$, $\omega$) may be determined by the coupled non-linear equations, $$\partial_t \omega + \partial_x \psi \partial_y \omega - \partial_y \psi \partial_x \omega = \nu_0 \nabla^2 \omega, \qquad (2.2a)$$

$$\nabla^2 \psi = \omega, \qquad (2.2b)$$

along with appropriate boundary conditions for $\psi$ and $\omega$. The initial state may be defined by a stream-vorticity field, $$\Sigma_0 \equiv (\psi_0(x,y), \omega_0(x,y)) = (\psi(0,x,y), \psi(0,x,y)), \qquad (2.3)$$

and solving the pair (2.1a, b) gives the future state $\Sigma_t = (\psi(t, x, y), \omega(t, x, y))$.

From knowledge of the vorticity, one can compute various other quantities of physical interest, such as the stream function $\psi(t, x, y)$, which solves Poisson's equation, (with an integral, i.e., non-local solution), $$\nabla^2 \psi = \omega, \psi = \text{constant on the boundary}, \qquad (2.4)$$

the velocity field, which for 2-d incompressible flow can be defined as, $$\vec{q} = \text{curl}(-\psi \hat{k}), \text{ for } \psi(t,x,y) \text{ defined in (2.4)} \qquad (2.5)$$

and the head of pressure $B = (p/\rho_0) + |\vec{q}|^2/2$, which solves another Poisson's equation, $$\nabla^2 B = \omega^2 - (\nabla \psi) \cdot (\nabla \omega), \partial_\tau B = (1/\nu_0) \partial_n \omega \text{ on the boundary}, \qquad (2.6)$$

where $\partial_\tau$ and $\partial_n$ denote the tangential and outward-normal derivatives, respectively. A thorough treatment of the inversion problem using the Biot-Savart law and Green's theorem is given in A. J. Majda, A. L. Bertozzi, *Vorticity and Incompressible Flow*, Cambridge UK: Cambridge University Press, 2002.

The vorticity may be specified on the boundary, which is equivalent to prescribing the wall shear stress (see G. -H. Cottet, P. D. Koumoutsakor, *Vortex Methods: Theory and Practice*, Cambridge UK: Cambridge University Press, 2000). The normal derivative of the stream function $\partial_n \psi = 0$ may not generally vanish in this approach, thus allowing slip on the boundary. This has already found application in some problems from oceanography (see P. Cessi, L. Thompson, 1990: Geometric control of the inertial recirculation, J. Phys. Oceanogr., 20, pp. 1867-1875). Also, see J. R. Holton, *An Introduction to Dynamic Meteorology*, Academic Press 1979, for further discussion on applications of (2.2 a, b) to meteorology and B. Mohammadi, O. Prionneau, *Analysis of the K-epsilon Turbulence Model*, John Wiley & Sons, Chichester England, 1994, for other issues on boundary conditions.

To obtain results using techniques of quantum mechanics, several assumptions may be made, resulting in a linear convection-diffusion model for the flow (see G. -H. Cottet, P. D. Koumoutsakor, Vortex Methods: Theory and Practice, Cambridge, UK: Cambridge University Press, 2000). The assumptions are as follows:

(A1) Potential (or laminar) flow dominates in the velocity field;

(A2) Boundary vorticity is time independent;

(A3) Interior vorticity perturbations are simple-harmonic in time;

(A4) Perturbations of streamlines are not reintroduced into the nonlinearities.

Assumption (A1) suggests the use of conformal transformations, in which potential flow is transformed into uniform flow. The conformal transformations may be considered optimal among all the coordinate transformations since they result in new analytic coefficients and terms in the transformed differential equations. Analyticity is a desired property for the application of complex scaling to the study of the flow equations. (A2) and (A3) are standard first order choices (see L. D. Landau, E. M Lifshitz, Fluid Mechanics, Oxford: Pergamon Press Ltd., 1959) and are imposed to allow a qualitative analysis of the flow problem. Finally, (A4) may only be reasonable for nearly-laminar low-Re flow where turbulent phenomena does not develop.

Imposing assumptions (A1)-(A4) on the study of equation (2.2a, b) can provide a spectral analysis of vorticity.

3. Flow Past A Circular Cylinder (a) Preliminaries: The Jacobian of a transformation from (x, y) coordinates to ($\xi, \eta$) coordinates may be denoted, $$J(\xi, \eta; x, y) \equiv \frac{\partial(\xi, \eta)}{\partial(x, y)} \equiv \partial_x \xi \partial_y \eta - \partial_y \xi \partial_x \eta. \qquad (3.1)$$

Then the vorticity equation in 2-dimensions, for $\omega = \Delta_{x,y} \psi$ can be written, $$\frac{\partial \omega}{\partial t} = -\frac{\partial(\psi, \omega)}{\partial(x, y)} + \nu_0 \Delta_{x,y} \omega. \qquad (3.2)$$

This section considers the potential flow past a circular cylindrical of radius $r_0 > 0$ where $\vec{q} \simeq U\hat{i}$ at large distance from the object. The far field conditions on the stream function and vorticity are, $$\psi(t,x,y) \sim -Uy, \omega(t,x,y) \sim 0, x^2 + y^2 \gg 1, \qquad (3.3a)$$

where in polar coordinates, $$x = r \cos \theta, y = r \sin \theta, r^2 = x^2 + y^2.$$

For this flow profile the velocity field may be considered symmetric about the x-axis, at least in the case of low Re, such as between about 4 and about 10. This breaks down near the object when oscillations appear for moderate Re values; however, symmetry may be assumed so the stream function and vorticity will be an odd function of x, satisfying the boundary conditions, $$\psi(t,x,y) = 0, \omega(t,x,y) = 0, \text{ for } y = 0 \text{ or } r = r_0 \qquad (3.3b)$$

To convert from the exterior of a cylinder $r > r_0$, to the entire two-dimensional plane (excluding a finite line segment), one defines the complex coordinates, $$z = x + iy, \zeta = \xi + i\eta, \qquad (3.3c)$$

and considers the mapping $\zeta = z/r_0 + r_0/z$, which in the 2-dimensional coordinates becomes, $$\xi = (x/r_0)(1 + r_0^2/r^2), \eta = (y/r_0)(1 - r_0^2/r^2). \qquad (3.4)$$

This transformation is uniquely invertible for $x^2 + y^2 > r_0^2$, and provides a mapping from the exterior of a cylinder onto all space in the ($\xi, \eta$) coordinates, except for the branch cut on the line $-2 < \xi < 2$, $\eta = 0$. Modified versions of the stream function and vorticity in these new coordinates, under assumptions (A1) and (A4), are taken to be, $$\Psi(\eta) \equiv \psi(t,x,y) = -U\eta, W(t,\xi,\eta) \equiv J^{-1} \omega(t,x,y), \qquad (3.5a)$$

where $I^2=J$ is the Jacobian of the coordinate transformation, $$I^2=J(\xi,\eta;x,y)=|d\zeta/dz|^2=r_0^{-2}(1+[r_0^4-2r_0^2(x^2-y^2)]/r^4) \quad (3.5b)$$

The vorticity equation becomes, $$\partial_t IW=-I^2(-\Psi'(\eta)\partial_\xi IW)+\nu_0 I^2\Delta_{\xi,\eta}IW. \quad (3.5c)$$

Using the approximation in (3.5a) one can derive a non-symmetric evolution equation, $$\partial_t W=(-U/2)(\partial_\xi I^2)W-UI^2(\partial_\xi W)+\nu_0 I\Delta_{\xi,\eta}IW. \quad (3.6)$$

To simplify this equation further, one can define the Reynolds number $Re=2r_0 U/\nu_0$ and assume a harmonic time dependence, $$W(t,\xi,\eta)=e^{-i\sigma\nu_0 t}W_p(\xi,\eta). \quad (3.7a)$$

Finally, one can ignore the advection term, $-UI^2(\partial_\xi W)$. The consequence is a symmetric Schrödinger equation, $$i\sigma W_p=H(Re)W_p, \quad (3.7b)$$

$$H(Re)=-(I\Delta_{\xi,\eta}I)+Re\,Vr_0(\xi,\eta), \quad (3.7c)$$

where H(Re) is a self-adjoint operator, referred to as the Hamiltonian. The potential function is $Vr_0(\xi,\eta)$ and depends on the radius $r_0$. The potential takes the form, $$Vr_0(\xi,\eta) = (\partial_\xi I^2)/(4r_0) \quad (3.7d)$$

$$= (-xx_\xi + 3yy_\xi)/(r^4 r_0) -$$

$$r_0(r_0^2 - 2x^2 + 2y^2)(xx_\xi + yy_\xi)/(r^6).$$

Figure 3:
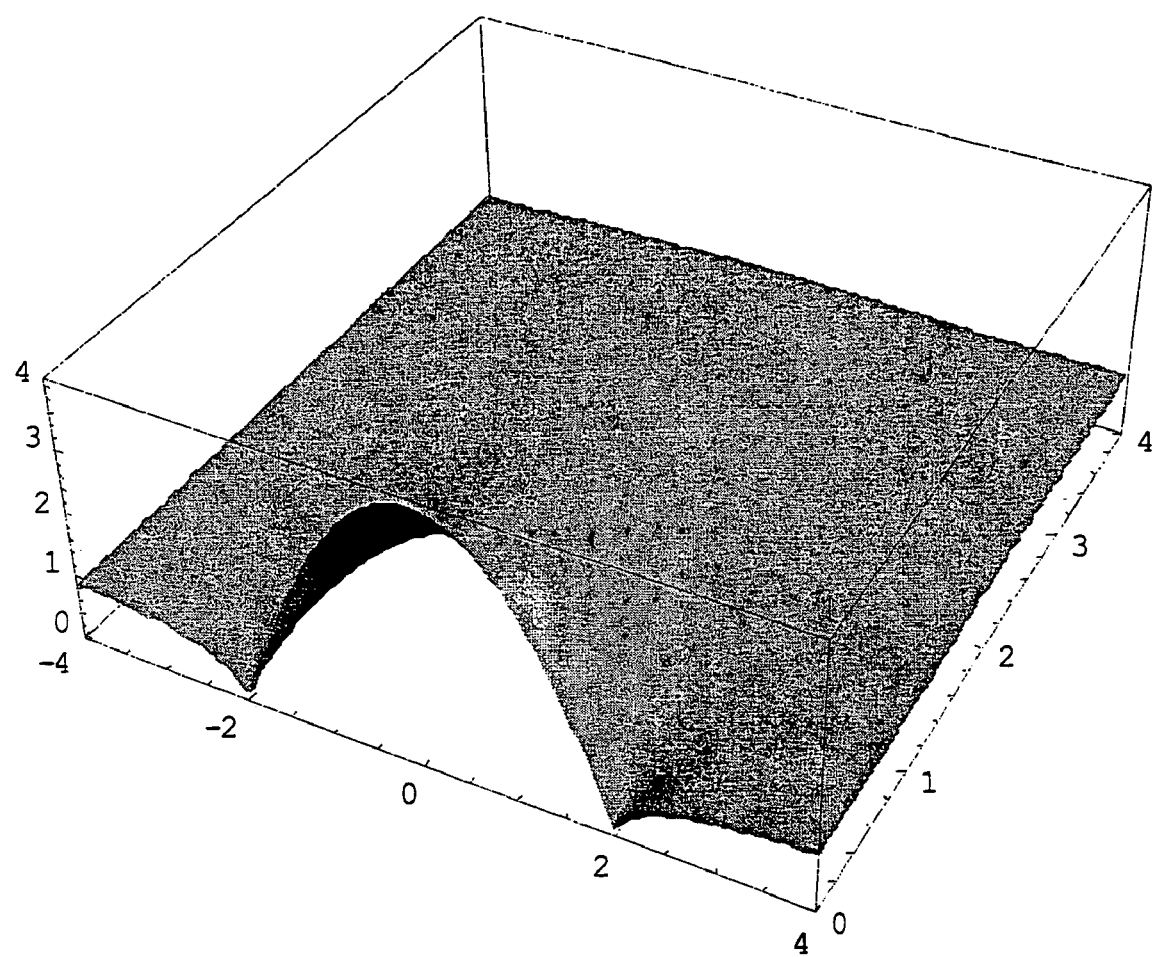
FIG. 3 is a contour graph of a potential function according to embodiments of the present invention.

FIG. 3 illustrates the contour of the potential function $Vr_0$ in (3.7d) in the Cartesian coordinates $(\xi,\eta)$.

The partial derivatives $x\xi$, $y\xi$ are obtained by differentiating (3.4) and solving, which gives, $$x\xi=r_0(r^4-r_0^2 x^2+r_0^2 y^2)/[(x^2-r_0^2)^2+y^2(2x^2+y^2+2r_0^2)]$$

$$y\xi=(-2r_0^3 xy)/[(x^2-r_0^2)^2+y^2(2x^2+y^2+2r_0^2)] \quad (3.7e)$$

The potential has two wells and two peaks at $\xi=\pm 2$, $\eta=0$. The downstream part of the well near $\xi\sim 2$ is the deepest part of the potential. One can obtain an antisymmetric bound state, similar to the vortex pair seen for small Re in experiments and numerical solutions, near $\xi=2$, $\eta=0$.

Theoretically, the spectrum of H(Re) must be real, with a continuous part being the subset $[0,\infty)$ of the real axis, and with some discrete negative eigenvalues, depending on the size of Re >0 (see M. Reed, B. Simon, *Methods of Modern Mathematical Physics LIV*, Academic Press, Inc., London Ltd., 1978-80). In the next section, negative eigenvalues are discussed, which due to (3.7a), may correspond to exponentially growing vortices. For real flows, the non-linear advection term controls the growth of vorticity by transporting circulation downstream. Thus, the wake region may remain of finite size for sufficiently small Re.

(b) Spectral Analysis—bound states: The onset of vortex separation in the wake region correlates with the appearance of the lowest negative eigenvalue for an anti-symmetric state, as shown below.

To find the bound states of the eigenvalue equation (3.7b) the projection method may be used. The notation of C. Cohen-Tannoudji, B. Diu, F. Laloë, *Quantum Mechanics*, Paris: Hermann Publishers, 1977 may be used. A collection of complete wave functions on the $(\xi,\eta)$ space can be chosen.

Note that symmetry about the $\eta$ axis is broken by the potential function near the strip $-2'\leq\xi\leq 2$, $\eta=0$. It may be sufficient to restrict to the half space $(-\infty,\infty)\times(0,\infty)$. Next, since localized states are of interest, one can work on a compact subset of the half plane, in particular, the rectangular $(\xi,\eta)$ region $[-X, X]\times[0,Y]$ for fixed $X,Y \in R^+$. Then one can define, $$\phi_{k,l}(\xi,\eta) \equiv (XY)^{-1/2} e^{i2\pi k\xi/X}\sin(2\pi l\eta/Y), \quad (3.7f)$$

$$I \equiv \sum_{k=-\infty}^{\infty}\sum_{l=1}^{\infty}|\phi_{k,l}\rangle\langle\phi_{k,l}|,$$

where I is the identity operator on square-integrable functions. The space of square-integrable functions is written simply as $L^2([-X,X]\times[0,Y])$. Multiplying both sides on the left of (3.7b) by I from (3.5b), applying the identity I between H(Re) and $IW_p$ in (3.7b), and multiplying the function $\phi_{k',l'}^*(\xi,\eta)$ on the left of (3.7b) (where * denotes complex conjugation), then integrating over $[-X,X]\times[0,Y]$, gives the equivalent matrix equation, $$i\sigma\langle\phi_{k',l'}|IW_p\rangle = \sum_{k=-\infty}^{\infty}\sum_{l=1}^{\infty}(\langle\phi_{k',l'}|-I^2\Delta_{\xi,\eta}|\phi_{k,l}\rangle\langle\phi_{k,l}|IW_p\rangle + Re \quad (3.8a)$$

$$\langle\phi_{k',l'}|V_\lambda|\phi_{k,l}\rangle\langle\phi_{k,l}|IW_p\rangle),$$

where in this section the notation $V_\lambda=Vr_0$ is used, and the $L^2$ inner product is written, $$\langle f|g\rangle \equiv \int_{\xi=-X}^{X}\int_{\eta=0}^{Y} f^*(\xi,\eta)g(\xi,\eta)d\xi d\eta. \quad (3.8b)$$

Now, once computed, the coefficients, $$C_{k,l}\equiv\langle\phi_{k,l}|IW_p\rangle, \quad (3.8c)$$

are used to reconstruct the vorticity and streamfunction profiles.

Using the fact that $I^2=1+O(r^{-2})$ as $r\to\infty$, one can rewrite the equation (3.7b) as, (3.9)

$$i\sigma C_{k',l'} = \sum_{k=-\infty}^{\infty}\sum_{l=1}^{\infty}([(k/X)^2+(l/Y)^2]\delta_{k',k}\delta_{l',l}C_{k,l} + \quad (3.9a)$$

$$[(k/X)^2+(l/Y)^2]\langle\phi_{k',l'}|(I^2-1)|\phi_{k,l}\rangle C_{k,l} + Re\langle\phi_{k',l'}|V_\lambda|\phi_{k,l}\rangle C_{k,l}),$$

where $\delta_{i,j}$ is the Kroneker delta. Defining, $$L_{k,l}\equiv(k/X)^2+(l/Y)^2, M_{k',l';k,l}\equiv\langle\phi_{k',l'}|(I^2-1)|\phi_{k,l}\rangle, N_{k',l';k,l}\equiv\langle\phi_{k',l'}|V_\lambda|\phi_{k,l}\rangle, \quad (3.9b)$$

gives the finite matrix equation, $$i\sigma C_{k',l'}=L_{k,l}\delta_{k',k}\delta_{l',l}C_{k,l}+L_{k,l}M_{k',l';k,l}C_{k,l}+Re\,N_{k',l';k,l}C_{k,l}. \quad (3.10a)$$

To obtain the $\sigma$'s numerically, a finite collection of functions can be used, and the corresponding coefficients can be evaluated.

Finally, to compare with the appearance of a downstream vortex, one can solve for the stream function, $$\Delta_{\xi,\eta}(\psi - U\eta) = \Gamma^{-1}W, \quad (3.10b)$$

which in the $(\xi,\eta)$-coordinates has boundary conditions, $$\psi = U\eta \text{ on } \partial([-X,X] \times [0,Y]). \quad (3.10c)$$

Using the projection method as above, one can obtain the equation, $$\sum_{k=-\infty}^{\infty}\sum_{l=1}^{\infty} L_{k',l'}\langle\phi_{k,l}|I^2|\phi_{k',l'}\rangle\langle\phi_{k',l'}|\psi\rangle = C_{k,l}, \quad (3.10d)$$

from which the stream function can be written in terms of $(\xi,\eta)$, $$\psi = U\eta + \sum_{k=-\infty}^{\infty}\sum_{l=1}^{\infty}\langle\phi_{k,l}|\psi\rangle e^{i2\pi k\xi/X}\sin(2\pi l\eta/Y). \quad (3.10e)$$

The function $\psi$ has a single extreme point in the flow region for all Re that are sufficiently large, such as between about 10 to 50, and this occurs behind and just downstream from the object, in agreement with experiment.

(c) Spectral Analysis—top resonances: In this section we use complex scaling in the $(\xi,\eta)$-plane is used to study the oscillating modes of the flow. Due to the singularities at $\xi=-2$ and 2 for $\eta=0$, the plane is divided into three regions $$R_1 \equiv \{(\xi,\eta)|\xi<-2\}, R_2 \equiv \{(\xi,\eta)|-2<\xi<2\}, R_3 \equiv \{(\xi,\eta)|2<\xi\}. \quad (3.10f)$$

Then for each $\theta \in \mathbb{C}$ one can define the variable transformation from $R^2 \to C^2$ as the vector function, (3.11)

$$\varphi_\theta(\xi,\eta) = (\xi_\theta, \eta_\theta) \equiv \begin{cases} (-2 + e^\theta(\xi+2), e^\theta\eta), & (\xi,\eta) \in R_1 \\ (3\xi/2 - \xi^3/8 - e^\theta(\xi/2 - \xi^3/8), e^\theta\eta), & (\xi,\eta) \in R_2 \\ (2 + e^\theta(\xi-2), e^\theta\eta), & (\xi,\eta) \in R_3 \end{cases}$$

and the corresponding Jacobian, $$\mathfrak{J}_\theta(\xi,\eta) \equiv det J(\xi_\theta,\eta_\theta;\xi,\eta) = e^{2\theta}(1+\chi_1(\xi,\theta)). \quad (3.11b)$$

Here the functions $\chi_1, \chi_2$, are defined that for $|\xi|<2$, $$\chi_1(\xi,\theta) \equiv e^{-\theta}\xi'_\theta - 1 = 3(e^\theta-1)\xi/(3(4-\xi^2) - e^\theta(4-3\xi^2)),$$

$$\chi_2(\xi,\theta) \equiv \xi''_\theta/(2\xi'_\theta) = -24\xi(1-e^\theta)/(3(4-\xi^2) - e^\theta(4-3\xi^2)), \quad (3.11c)$$

and vanish for $|\xi|>2$ or $\theta=0$. Note that $\chi_1$ is continuous and $\chi_2$ is bounded both for $\theta$ in a restricted neighborhood of $0 \in \mathbb{C}$. Now one can obtain the induced transformation $U_\theta$ which acts on functions $\psi$ as, $$U_\theta\psi(\xi,\eta) \equiv \mathfrak{J}_\theta^{1/2}\psi(\vec{\Phi}_\theta(\xi,\eta)), \quad (3.11d)$$

and on multiplicative-differential operators A as, $$A_\theta\phi \equiv U_\theta A U_\theta^{-1}\phi \text{ or } A_\theta U_\theta\psi = U_\theta A\psi. \quad (3.11e)$$

For the Hamiltonian the transformation gives the family of operators, $$H_\theta(\text{Re}) = -e^{-2\theta}I_\theta(\partial_\xi + \chi_2(\xi,\theta))(1+\chi_1(\xi,\theta))^{-2}(\partial_\xi + \chi_2(\xi,\theta)) - \quad (3.12a)$$
$$e^{-2\theta}I_\theta\partial_\eta^2 I_\theta + \text{Re}V_{\lambda,\theta}(\xi,\eta).$$

Figure 4:
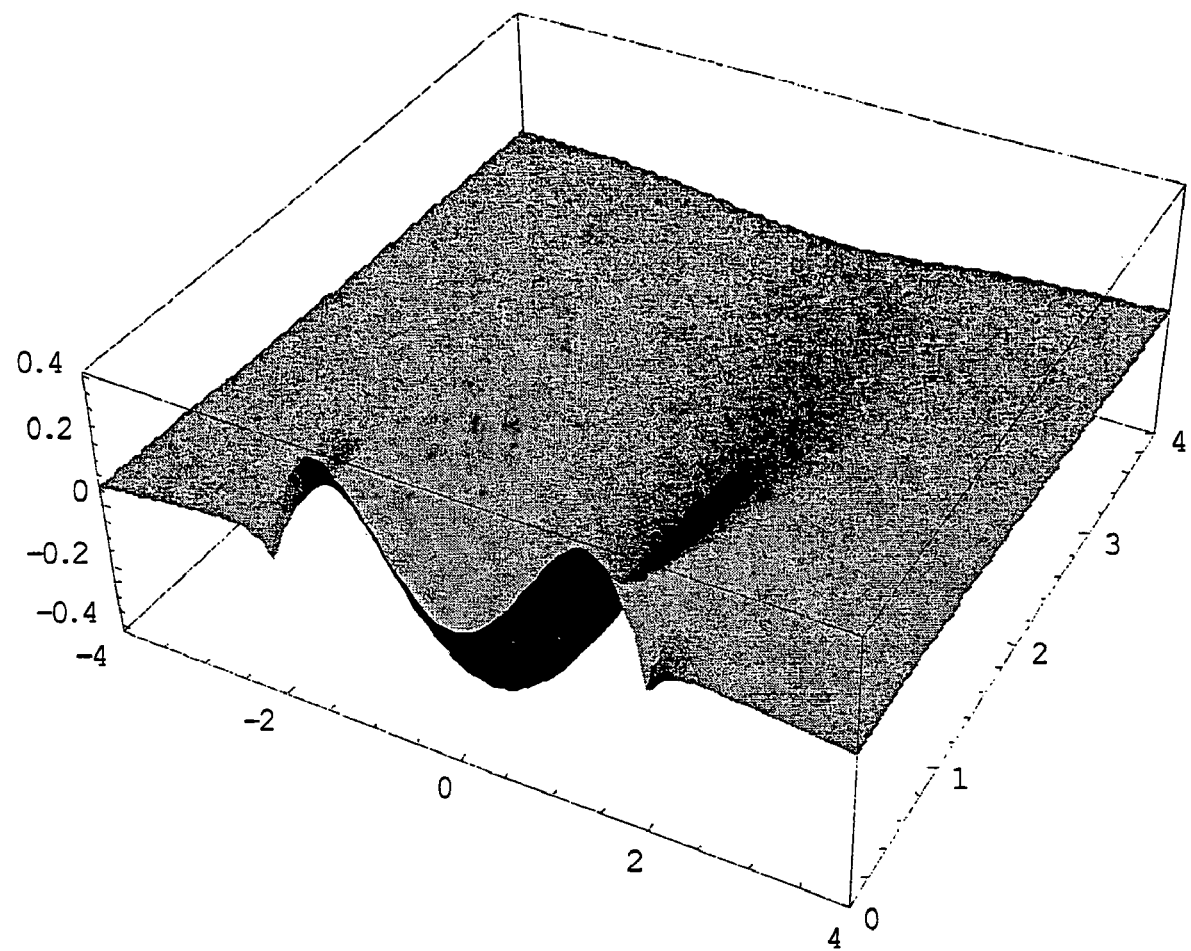
FIG. 4 is a contour graph of the imaginary part of the potential function of FIG. 3 for $\theta = \pi/8$.

The real part of the potential may not change significantly with scaling, but the imaginary part is no longer zero everywhere. FIG. 4 illustrates the contour of the imaginary part of the potential $V_{\lambda,\theta}(\xi,\eta)$ for $\theta=\pi/8$.

In order for $H_\theta(\text{Re})$ to make sense, conditions of smoothness must be satisfied by the potential $V_\lambda$ and the Jacobian $I^2$ and this is resolved by the use of a conformal transformation. There are two singularities to be concerned with, at $\xi=\pm 2$ for $\eta=0$, and this is the reason for the choice of the variable transformation in (3.11a). By this choice, however, one is restricted in the values of complex $\theta$ that can be used. Also note that since $\xi_\theta$ is only twice differentiable, so one may define $H_\theta(\text{Re})$ as a quadratic form, which is sufficient in this analysis. (Details will not be considered here but for a thorough discussion see W. Hunziker, *Distortion analyticity and molecular resonance curves*, Ann. Inst. Henri Poincaré, Vol.45(4), 1986, pp.339-358.)

By defining the vector components, $$C_{k,l}^\theta \equiv \langle\phi_{k,l}|I_\theta W_p\rangle, \quad (3.12b)$$

and the matrix elements, $$P_{k',l';k,l}^\theta \equiv \langle\phi_{k',l'}|((i2\pi k'/X)+\chi_2)I_\theta^2(1+\chi_1)^{-2}((i2\pi k/X) - \chi_2)|\phi_{k,l}\rangle, \quad (3.12c)$$

$$Q_{k',l';k,l}^\theta \equiv -4\lambda\langle\phi_{k',l'}|V_{\lambda,\theta}(1+\chi_1)^{-1}((i2\pi k/X)-\chi_2)|\phi_{k,l}\rangle$$

$$M_{k',l';k,l}^\theta \equiv \langle\phi_{k',l'}|(I_\theta^2-1)|\phi_{k,l}\rangle, N_{k',l';k,l}^\theta \equiv \langle\phi_{k',l'}|V_{\lambda,\theta}|\phi_{k,l}\rangle,$$

one can obtain the complex-scaled matrix equation $$ie^{2\theta}\sigma_\theta C_{k',l'} = (P_{k',l';k,l}^\theta + Q_{k',l';k,l}^\theta)C_{k,l} + \quad (3.13)$$
$$((2\pi l/Y)^2(\delta_{k',k}\delta_{l',l} + M_{k',l';k,l}^\theta) + \text{Re } e^{2\theta}N_{k',l';k,l}^\theta)C_{k,l}.$$

The kinetic term for the $\xi$-variable may become considerably more complicated from the application of complex scaling, but it can be rewritten as a perturbation of the expression in (3.10) for small $\theta \in \mathbb{C}$. Also note that some boundary terms have been ignored which we justify by the approximations, for $\xi=\pm X$, $$(I_\theta/\xi_\theta)\sim e^{-\theta}, \partial(I_\theta^2)/\partial\xi\sim 0. \quad (3.14)$$

The spectral values $\sigma\theta$ in (3.13) are either part of the continuous spectrum or part of the discrete spectrum. The zero value and those values that move continuously with changes in $\theta$ are in the continuous spectrum of $H\theta(\text{Re})$. The values that are stationary, or stationary once revealed, may be part of the discrete spectrum. The latter values are discussed below, in particular, how these values behave with respect to the coupling parameter Re, the addition of the advection term and the addition of non-linearities. This is examined in the next section.

Figure 5:
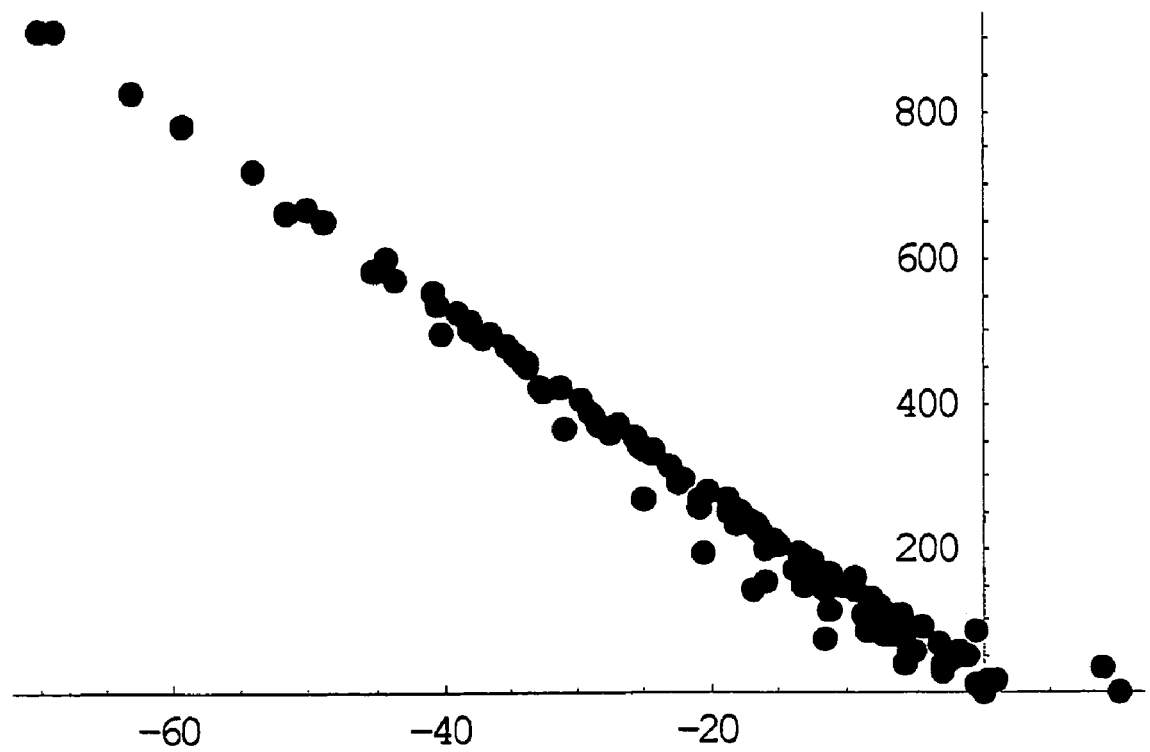
FIGS. 5 is a graph of bounded-state eigen values for a Reynold's number of 50 according to embodiments of the present invention.

4. Results (a) Eigenvalues: Solving equation (3.10) for θ=0 gives the appearance of positive eigenvalues. These correspond to bound states that grow. The inclusion of advection and non-linearities may keep this growth in check. FIG. 5 illustrates the appearance of bounded-state eigenvalues on the right hand side for Re=50. The bounded-state eigenvalues are not affected by the change in angle θ, however the growth-rate parameter iσ increases for the most stable vortex as Re increases.

Figure 6:
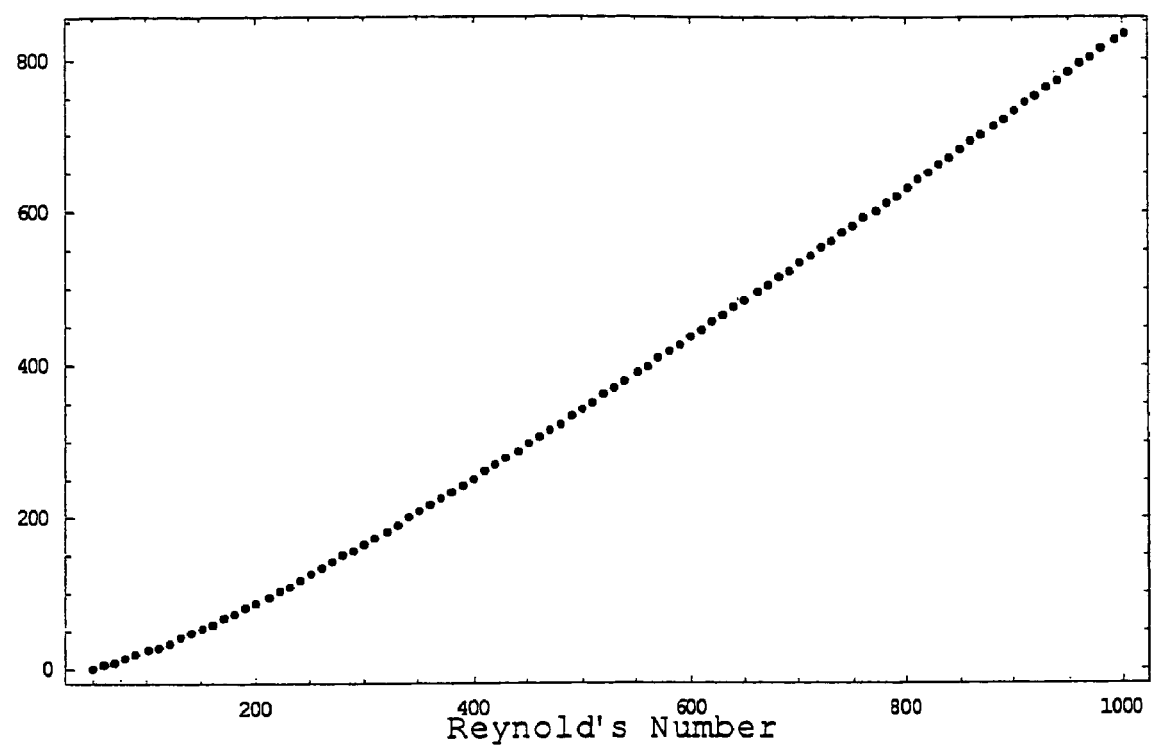
FIG. 6 is a graph of the dependence of growth rate of stable downstream vortex on the Reynold's number according to embodiments of the present invention.

FIG. 6 illustrates the dependence of the maximal growth rate $S_{max}$ of a stable downstream vortex on Re. There is a cutoff that occurs at low Re, at about 50, similar to what is typically observed in practice.

Figure 7:
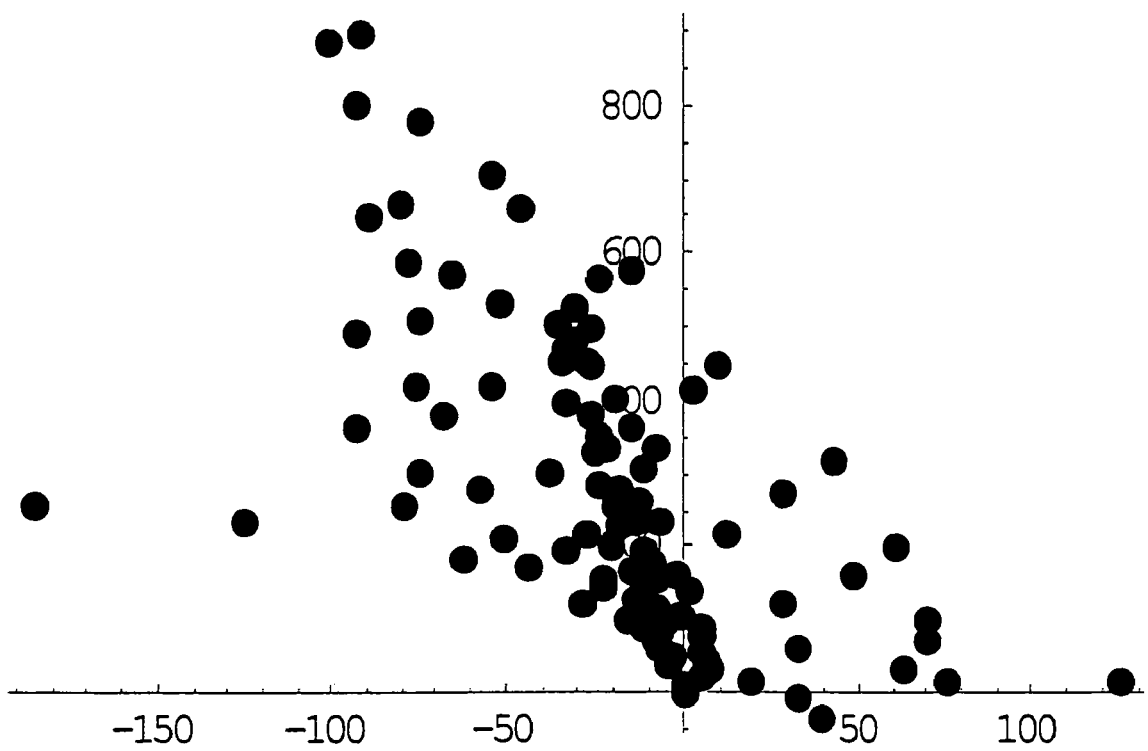
FIG. 7 is a graph of the appearance of resonances due to complex scaling according to embodiments of the present invention.

(b) Resonances: As θ ∈ C is increased along the imaginary axis some values of iσ move, while others remain relatively stationary. The stationary values are the eigenvalues and resonances of the system. In particular, complex iσ corresponds to wave motion in the flow region. FIG. 7 illustrates the appearance of resonances due to complex scaling.

EXAMPLE 2

Top Resonances of a Stenotic Flow Channel Line-perturbation Model

The linearized convection-diffusion model for incompressible flow through a channel with stenosis is discussed. Assuming simple harmonic motion with frequency $\lambda v_0$ and uniform background flow $\vec{u}_0(x,y)$, the equation for vorticity perturbation ω(t, x, y) becomes, $$i\lambda\omega = -\Delta\omega - (1/v_0)\vec{u}_0 \cdot \nabla\omega, -\infty < x < \infty, |y| \to h \text{ as } |x| \to \infty.$$

Applying a conformal transformation $\zeta(z)=\xi(x,y)+i\eta(x,y)$ to a perturbed channel region can provide an equivalent equation in new ξ,η-coordinates, $$-\Delta\omega + (i\lambda/J)\omega = (Re/2h)^2\omega, -\infty < \xi < \infty, -1 < \eta < 1,$$

where $J \equiv |\zeta'(z)|^2$ is the Jacobian of the transformation. A model may be presented which reveals that the system has two quantum wells, corresponding to bound states, and a quantum (top resonance) peak implying the existence of top resonances. It is demonstrated that there are families of spectral resonances. For example, complex frequencies occurs at $$f_{0,n} = \lambda_0 v_0 \exp(i\beta_n),$$

where the coefficient is $$\lambda_0 = (Re/2h)^2 \exp[-2h\kappa/3]$$

and where the exponent is, $$\beta_{0,n} \sim 2 \arccos[(h\kappa)^{1/2} \exp[-h\kappa/3](2n+1)/Re],$$

where n=0, 1, 2, ... M. Here M is an upper limit on the number of frequencies.

Here k is the curvature of the boundary perturbation, h is the half-width of the channel and $U_0 = |\vec{u}_0|$ is the magnitude of the background flow velocity. A modification of the standard complex scaling technique may be used for the analysis.

1. Introduction

The Schrödinger-Vorticity equation is discussed as follows:

$$-\Delta_{\xi,\eta}\Phi + (i\lambda/J)\Phi = -(Re/2h)^2\Phi, \tag{1.1}$$

for smooth Φ supported in the region |ξ|<∞, |η|<1 where the potential function is defined in terms of $J \equiv |\zeta'(z)|^2$, for, $$\zeta(z) \equiv \xi(x,y) + i\eta(x,y) \tag{1.2}$$

$$= \frac{z}{h} e^{m/(1+z^2/p^2)}$$

$$\equiv \frac{x+iy}{h} \exp\left(\frac{mp^2}{p^2+(x+iy)^2}\right).$$

Figure 8:
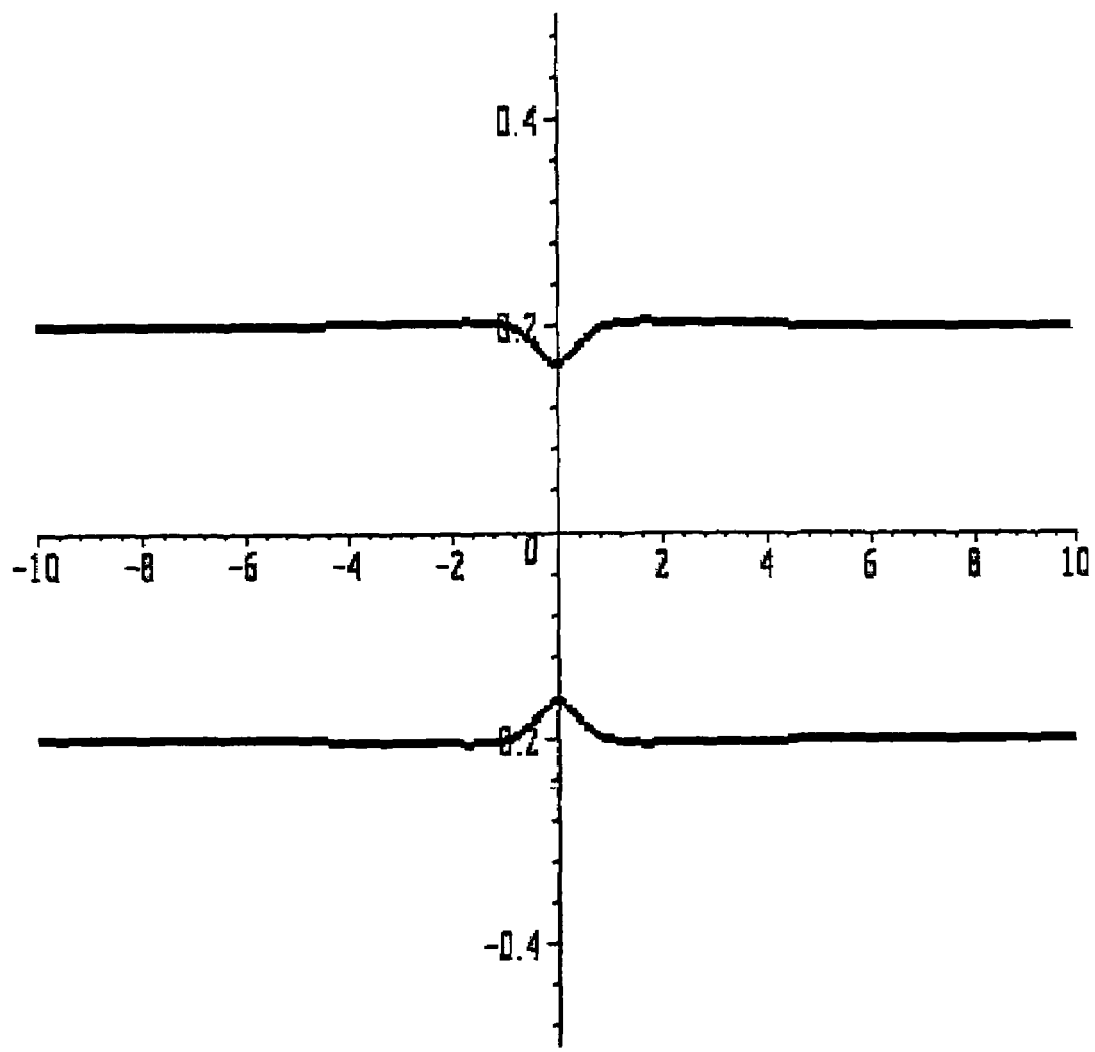
FIG. 8 is a graph of the shape of a channel boundary with stenosis according to embodiments of the present invention.

The actual region of interest corresponds to a perturbed channel in the variable z=x+iy. FIG. 8 shows the shape of channel boundary with stenosis, i.e. for m>0.

In (1.1) Re represents the Reynolds number of the flow and λ is related to the "degrees of freedom" of the system, which will be called "resonance frequencies". The channel region can be described by h>0, the (asymptotic) half-width parameter, m∈R, a boundary-perturbation shape parameter that roughly corresponds to the width or extent of the perturbation, and p>0, a perturbation-thickness parameter roughly corresponding to the height of the perturbation. In particular, (the channel width variable) |y|→h as (the channel length variable) |x|→∞ with |η|=1. The transformation (1.2) can provide a range of 2-dimensional models for flows through stenotic (m>0) or aneuritic (m<0) channels whose fluid equation, in the x, y-coordinates, is assumed to be, $$\partial_t \omega + \vec{u}_0 \cdot \nabla\omega = v_0 66 \omega, \tag{1.3}$$

where ω(t, x, y) is the vorticity and $\vec{u}_0$ is the steady background flow velocity ($\vec{u}_0 \sim U_0 \hat{i}$ for |x| large). The flow region is within the bounding curves, $$\pm 1 = \eta = Im[(z/h)\exp(mp^2/(p^2+z^2))], \tag{1.4}$$

so that at x=0, the transcendental equation can be obtained, $$y = \pm h \exp(-mp^2/(p^2+y^2)). \tag{1.5}$$

For a typically observed type of stenosis, p>>h (i.e., large width to height ratio of the stenosis, such as ratios between about 5 to 10 and thus one obtains the constriction points to be at $y \approx \pm h e^{-m}$. See J. Ryval, A. G. Straatman, D. A. Steinman, Low Reynolds Number Modeling of Pul-satile Flow in a Moderately Constricted Geometry, 11th Ann. Conf. CFD Soc. Canada, Vancouver, May 2003. The curvature of the perturbation can be considered as follows:

$$\kappa \approx 6me^m h/p^2, \text{ for } p >> h. \tag{1.6}$$

The parameters h, p and m may be determined from measurements of the frequencies produced by the perturbation. This task may use a new perspective on the creation of both the stable downstream vortices and the oscillatory von Kármán vortex street. For a history of the problem see L. D. Landau, E. M Lifshitz, *Fluid Mechanics*, Oxford: Pergamon Press Ltd., 1959, K. E. Gustarson, J. A. Sethian, *Vortex Methods and Vortex Motion*, SIAM, Philadelphia Pa., 1991, M. Griebel, T. Dornseifer, T. Neunhoeffer, *Numerical Simulation in Fluid Dynamics: A Practical Introduction*, SIAM Monographs, Philadelphia Pa., 1997, B. Mohammadi, O. Pironneau, *Analysis of the K-epsilon Turbulence Model*, John Wiley & Sons, Chichester England, 1994.

Some difficulties in explaining low to moderate ranged Reynolds number phenomena may be attributed to the non-linearity of the basic fluid equations. However, in the presence of a background uniform flow, bounded by rigid walls, the non-linear effects may either decay in time or may be carried downstream. A particular application can be found in the study of blood flow through partially-blocked arteries where, due to the pulsatile nature of the flow, high Re values may be short lived and, therefore, non-linearities may play a minor role. The von Kármán street, which may be considered primarily as a linear effect, applies an oscillating sheer stress to the artery walls that can result in a low frequency vibration. Without wishing to be bound by theory, it is speculated that this may be the main mechanism behind bruits. (See C. G. Caro, T. J. Pedley, R. C. Schroter, W. A. Seed, *The Mechanics of the Circulation*, Oxford: Oxford University Press, 1978.)

The analysis herein may demonstrate that there can be resonance states concentrated in the central region of the channel if there is a stenosis. For both stenosis and aneurisms, the theory discussed herein may also predict the presence of stable vortex states, visible using ultrasound.

For example, consider a 2-dimensional fluid with kinematic viscosity $v_0>0$, and uniform background speed $U_0>0$, flowing through a channel bounded by the curved defined in (1.4). Then, imposing Dirichlet boundary conditions on the Schrodinger-Vorticity equation (1.1) gives, for m>0, a finite family of spectral resonances $\{f_{l,n}\}$ where $\exists L, M \geq 0$ so that $$f_{l,n} = \lambda_l v_0 \exp[i\beta_{l,n}] \text{ with } \lambda_l \approx \exp[-2h\kappa/3](Re/2h)^2 \quad (1.7a)$$

and where, $$\beta_{l,n} \approx 2 \arccos[-(h\kappa)^{1/2}\exp[-2ml/(2n+1)/(2h(\lambda_l)^{1/2})]], \quad (1.7b)$$

for l=0, 1, 2, ... L, n=0, 1, 2, ... M. Furthermore, the corresponding vortex-resonance states may be concentrated along the centerline y=0, with an approximate form, $$\omega_{l,n}(t,x,y) \approx e^{i f_{l,n} t} P_n(x) e^{(Re/2)x/h} \exp\{-\sqrt{\lambda_l h\kappa} x^2/2\} \cos((2l+1)\pi y/2h), \quad (1.8)$$

where $P_n(x)$ is an $n^{th}$ degree polynomial in the variable x.

Example 2 is organized as follows. In section 2, standard definitions and notations used in the study of the fluid equations are discussed. The usual Schrödinger equation is studied and the equations (1.7a-b) and (1.8) are verified. By symmetry considerations, the problem may be made one-dimensional. Section 3 of Example 2 contains a discussion on the consequences of these results.

2. The Fluid Equations in a 2-Dimensional Channel

The stream-vorticity equations for 2-dimensional flow are, $$\partial_t \omega + \partial(\psi, \omega)/\partial(x, y) = v_0 \Delta_{x,y} \omega, \quad (2.1a)$$

$$\Delta_{x,y}\psi = \omega. \quad (2.1b)$$

Here the Jacobian is defined as, $$\partial(\psi,\omega)/\partial(x,y) = \partial_x\psi\partial_y\omega - \partial_y\psi\partial_x\omega. \quad (2.1c)$$

By performing the conformal transformation (1.2) and assuming a simple-harmonic time dependence, solutions may be provided having the form:

$$\omega(x,y,t) = e^{i\lambda v_0 t} e^{(Re/2)\xi} W(\xi,\eta). \quad (2.2)$$

Substituting into (2.1a) gives the corresponding equation, $$-\Delta_{\xi,\eta}W + (i\lambda/J)W = e^{-(Re/2)\xi}\partial(\psi, e^{(Re/2)\xi}W)/\partial(\xi,\eta), \quad (2.3a)$$

where the Jacobian function is computed from (1.2) to be, $$J \equiv \frac{\partial(\xi, \eta)}{\partial(x, y)} \quad (2.3b)$$

$$= \frac{1}{h^2} \frac{|p^4 + 2(1+m)p^2 z^2 + z^4|^2}{|p^2 + z^2|^4}$$

$$\exp\left\{\frac{-2mp^2(p^2 + x^2 - y^2)}{|p^2 + z^2|^2}\right\}.$$

Figure 9:
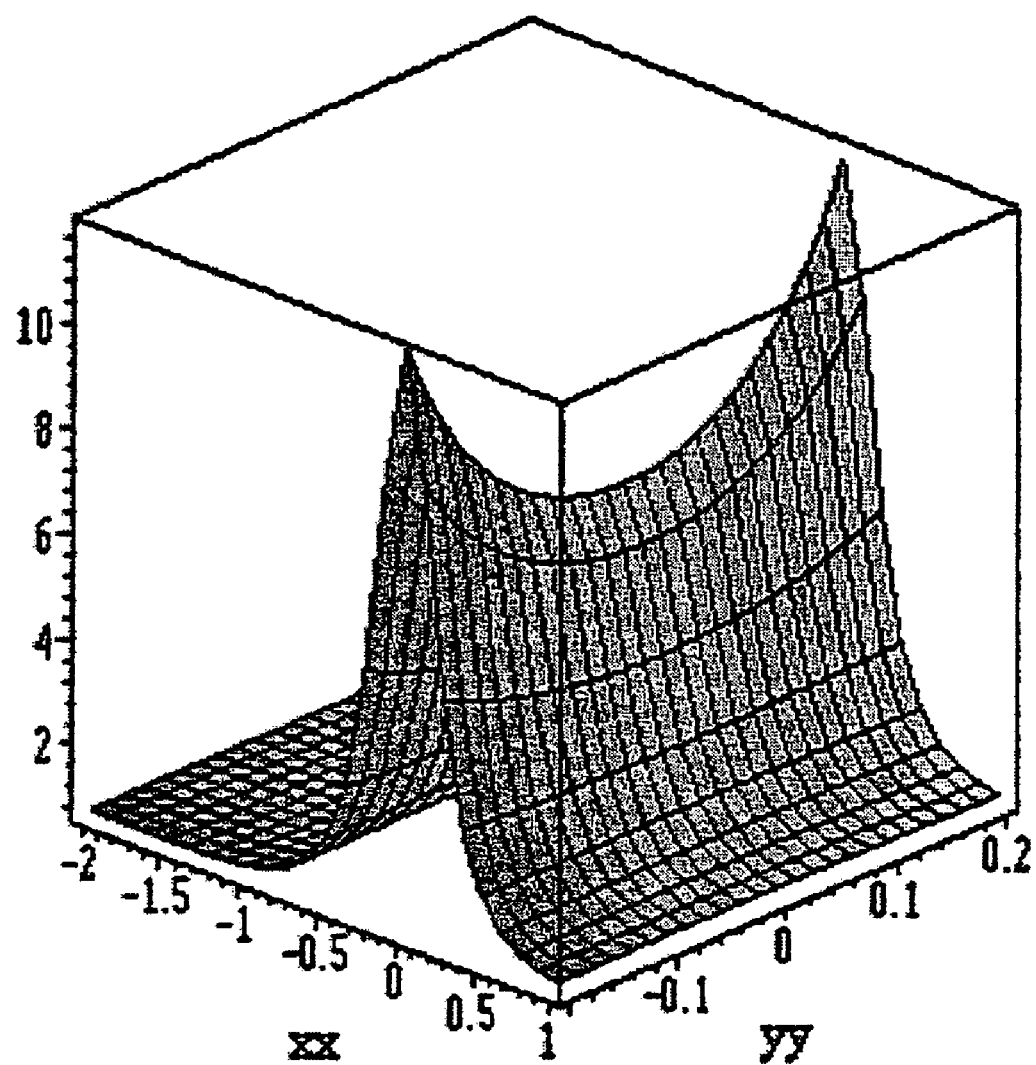
FIG. 9 is a graph of the shape of a potential reciprocal Jacobian for a boundary with stenosis according to embodiments of the present invention.

This complicated function may be analytic in both the x and y variables, and since the transformation $\zeta(z)$ is conformal, J is also analytic as a function of $\xi$ and $\eta$. FIG. 9 illustrates the shape of potential 1/J for a boundary with stenosis, i.e., for m>0.

At this point the search for solutions can be restricted (2.3a) to smooth functions defined on the strip region, $$R = \{(\xi,\eta) | -\infty < \xi < \infty, -1 < \eta < 1\}, \quad (2.3c)$$

which satisfy the Dirichlet boundary condition that $W(\xi, \pm 1) = 0$. Next a uniform background flow can be chosen, here expressed in $\zeta$ coordinates as, $$\vec{u}_0 = \text{curl}(-\psi \hat{k}), \psi = -U_0 h\eta. \quad (2.4)$$

Then using $Re \equiv U_0 h/v_0$ and (2.4) in (2.3a) gives the Schrödinger equation, $$-\Delta_{\xi,\eta}W + (i\lambda/J)W = -(Re/2)^2 W. \quad (2.5a)$$

(a) iλ Real

The (bounded-states) potential, $$V_b(\xi,\eta) = J^{-1}(\xi,\eta) - h^2, \quad (2.5b)$$

may be smooth and short-ranged, i.e., $|V_b| = O(1/|z|^2)$. There can be no $L^2(R)$ or $L^\infty(R)$ eigensolutions of (2.5a) for iλ<0. This suggests that there are no purely growing vortices in the flow region, as is known to be the case for real flows.

For iλ<0, plane wave solutions do exist. For iλ ∈ (−∞,−(Re/2h)²), bound-state solutions are possible for iλ ∈ (−(Re/2h)², 0). This is shown by rewriting (2.5a) as, $$-\Delta_{\xi,\eta}W + i\lambda V_b(\xi,\eta)W = -[i\lambda h^2 + (Re/2)^2]W. \quad (2.6)$$

Both the plane-wave and bounded states decay over time; however, in real flows, they may constantly being restimulated by boundary perturbations and non-linear effects.

The bound states may decay slower than the plane waves and may not even exist for Re>0 sufficiently small, for example, for Re between about 4 to 10. This cutoff effect is well known for the stable attach vortex, which appears downstream of a perturbation. For sufficiently large Re (between about 10 to 50), a small vortex may appear upstream from the perturbation as well.

(b) iλ Complex

Now consider the (resonance) potential, $$V_r(\xi,\eta) = J^{-1}(\xi,\eta) - J_m^{-1}, J_{m=}(0,0) = e^{-2m}/h^2, \quad (2.7a)$$

which has a saddle at the origin with $V_r(0,0)=0$. The behavior near the origin may be computed to be, $$V_r(\xi, \eta) = -A\xi^2 + B\eta^2 + O(\xi^3, \xi^2\eta, \xi\eta^2, \eta^3), \tag{2.7b}$$

$$A = h^3\kappa, \quad B = mh^4/p^2.$$

The equation studied is, $$-\Delta_{\xi,\eta} W + i\lambda V_r(\xi,\eta)W = -[i\lambda h^2 e^{2m} + (Re/2)^2]W. \tag{2.8a}$$

Since A in (2.7b) is positive, and $V_r$ may be considered (mostly) negative away from the origin of the perturbation with asymptotic value of $-1$, bound states may not be expected, but resonance states may be possible. To find the resonances the $\xi$-variable is scaled into the complex plane, $$\vec{\Phi}_\theta : R^2 \to C^2, \vec{\Phi}(\xi,\eta) = (e^\theta \xi, \eta), \tag{2.8b}$$

for $\theta \in C$. Then one can obtain the transformation on functions $W \in L^2(R)$, $$U_\theta W(\xi,\eta) = e^{\theta/2} W(e^\theta \xi, \eta), \tag{2.8c}$$

which is unitary for $\theta \in R$. Applying $U_\theta$ to both sides of (2.8a) gives, for $W_\theta = U_\theta W$, $$-e^{-2\theta}\partial_\xi^2 W_\theta - \partial_\eta^2 W_\theta + i\lambda V_r(e^\theta \xi, \eta)W_\theta = -[i\lambda h^2 e^{2m} + (Re/2)^2]W_\theta. \tag{2.9a}$$

Now one looks for square-integrable Solutions. A first approximation involves using the expansion in (2.7b) and choosing a vorticity boundary condition. Here, by assuming $W_\theta(\xi, \pm 1) = 0$, one can obtain a family of approximate separable solutions, $$W_\theta(\xi,\eta) \sim W_l(\xi;\theta)\cos[(2l+1)(\pi\eta/2)] \tag{2.9b}$$

for $|A|>>|B|$, with $l=0, 1, 2, \ldots L$. Then, as a function of $\xi$, We solves the 1-dimensional version of (2.9a), $$-e^{-2\theta}W_l'' + i\lambda A e^{2\theta}\xi^2 W_l = -[(2l+1)^2\pi^2/4 + i\lambda h^2 e^{2m} + (Re/2)^2]W_l. \tag{2.10a}$$

Standard numerical methods may provide approximations for solving the problem. For example, one finds a family of spectral resonances, with $L^2(R)$ solutions $W_l$, by imposing symmetry conditions. In particular, (2.10a) may be multiplied by $e^{2\theta} W_l$ and integrated over R. Then the spectral values may be expressed as, $$i\lambda = \lambda_l e^{i\beta_{l,n}}. \tag{2.10b}$$

Next, $i\beta_{l,n}$ can be set as $i\beta_{l,n} = -4\theta$ and the imaginary part of the resulting expression examined. This gives the condition, $$-\lambda_l h^2 e^{2m} \sin(2\beta_{l,n}) + [(2l+1)^2\pi^2/4 + (Re/2)^2] \sin(2\beta_{l,n}) = 0. \tag{2.10c}$$

For $\sin(2\beta_{l,n}) \neq 0$ is obtained the equality, $$\lambda_l = [(2l+1)^2\pi^2/4 + (Re/2)^2]e^{-2m}/h^2. \tag{2.11a}$$

Hence all frequencies $f_{l,n}$ may be restricted to a circle of radius $\lambda_l v_0$ in the complex plane. The eigensolutions have the form, for $n=0, 1, 2, \ldots M$, $$W_l(\xi,\eta) = H_n(\sqrt{\lambda_l h^3 \kappa}\xi)\exp\{-\sqrt{\lambda_l h^3 \kappa}\xi^2/2\}, \tag{2.11b}$$

where $H_n(x)$ are $n^{th}$ degree Hermite polynomials in x. The corresponding frequencies for this simple harmonic motion are obtained from, $$\sqrt{\lambda_l h^3 \kappa}(2n+1) = [(2l+1)^2\pi^2/4 + \lambda_l h^2 e^{2m} + (Re/2)^2]\cos(2\beta_{l,n}), \tag{2.11c}$$

from which one can solve for $\cos(\beta_{l,n})$ and obtain using (2.11a), $$\beta_{l,n} \sim 2 \arccos[-(h\kappa)^{1/2}(2n+1)/(2(\lambda_l)^{1/2}h \, e^{2m}))], \tag{2.11d}$$

Once a resonance has been found for any angle, in this case $i\beta_{l,n} = -4\theta$, it can exist for all larger angles (see W. Hunziker, *Distortion analyticity and molecular resonance curves*, Ann. Inst. Henri Poincaré, Vol. 45(4), 1986, pp. 339-358; B. Mohammadi, O. Pironneau, *Analysis of the K-epsilon Turbulence Model*, John Wiley & Sons, Chichester England, 1994).

3. Discussion of Results

In the previous section it was determined that frequencies may be restricted to a circle in the complex plane with radius $\lambda_l$. The angular position of these values in the complex plane can be determined by $\beta_{l,n}$ which may be determined from the equation, $$\cos(\beta_{l,n}/2) = [-(h\kappa)^{1/2} e^{-m}(2n+1)]/[(2l+1)]/[(2l+1)^2\pi^2 + Re^2]^{1/2}. \tag{2.11e}$$

However, equation (2.11e) cannot be solved if the expression on the right hand side has modulus greater than 1. Hence one obtains the cutoff condition, for $n=0$, and using the expression for $\lambda_0$, that, $$Re \geq [h\kappa e^{-2m}(2n+1)^2 - (2l+1)^2\pi^2]^{1/2}. \tag{2.11f}$$

For large perturbations one obtains the approximate condition that $$Re \geq \sqrt{h\kappa} e^{-m}(2n+1).$$

The numerical procedures used can involve choosing appropriate basis functions and computing matrix elements. The clear presence of resonances restricted to a circle may be found. By normalizing the results, resonances can be found that lie on a circle or ellipse (or elliptical curve). FIG. 10 illustrates resonances from the numerical procedure for Re=50, with an angle $\pi/6$ for a boundary with stenosis, i.e., for $m>0$.

For cylindrically symmetric stenosis in 3-dimensional arterial flow, one may obtain qualitatively similar results to those above. The work involves a restriction to the upper-half plane, $y>0$ and extra terms in equation (1.1). These terms are first order differential operators that may not drastically change the nature of the system.

EXAMPLE 3

Sample Analysis of Applicable Frequency Range for Peak-perturbation Model and Line-perturbation Model a) Peak-perturbation case: The von Kármán street is understood heuristically through the relation, $$f = 0.212 \, U_0/(2r_0), \tag{3.1}$$

where $U_0$ is the flow speed, $r_0$ is the radius of the perturbation, 0.212 is the Strouhal number for a cylinder, and f is the frequency of the corresponding wave observed downstream. The waves caused by flow past this object may move side-to-side. In the case of arterial flow one may expect ranges of, $$0 \leq U_0 \leq 30 \text{ cm/s}, 0 \leq r_0 \leq 1 \text{ cm}, \tag{3.2}$$

and thus the frequency can take on any positive value. However, in the typical steady state, moderate perturbation case it may be expected that, $$10 \text{ cm/s} \leq U_0 \leq 20 \text{ cm/s}, 1 \text{ mm} \leq r_0 \leq 5 \text{ mm}, \tag{3.3}$$

and this gives 10 Hz≦f≦100 Hz, corresponding to ULF waves. This is within the range of what was obtained in Example 1.

b) Line-perturbation case: In Example 2, the formula was obtained for the main frequency radius:

$$\lambda_0 = e^{-2h\kappa/3}(Re/2h)^2, \quad (3.4)$$

where h is the thickness parameter of the channel, κ is the radius of curvature of the perturbation and Re is the Reynolds number. To make a comparison with the above calculation, the frequency is $f=\lambda_0 v_0$ where $v_0$ is the kinematic viscosity. For arterial blood flow, typically $$Re \sim 1000, v \sim 0.01 \text{ cm}^2/\text{s}, h \sim 1 \text{ cm}, \kappa \sim 1/(1 \text{ mm}), \quad (3.5)$$

from which one can estimate hκ~10. Then, $$f \sim (e^{-2(10)/3}(1000/2)^2)0.01 \text{ cm}^2/\text{s} = 3 \text{ Hz}. \quad (3.6)$$

Figure 17:
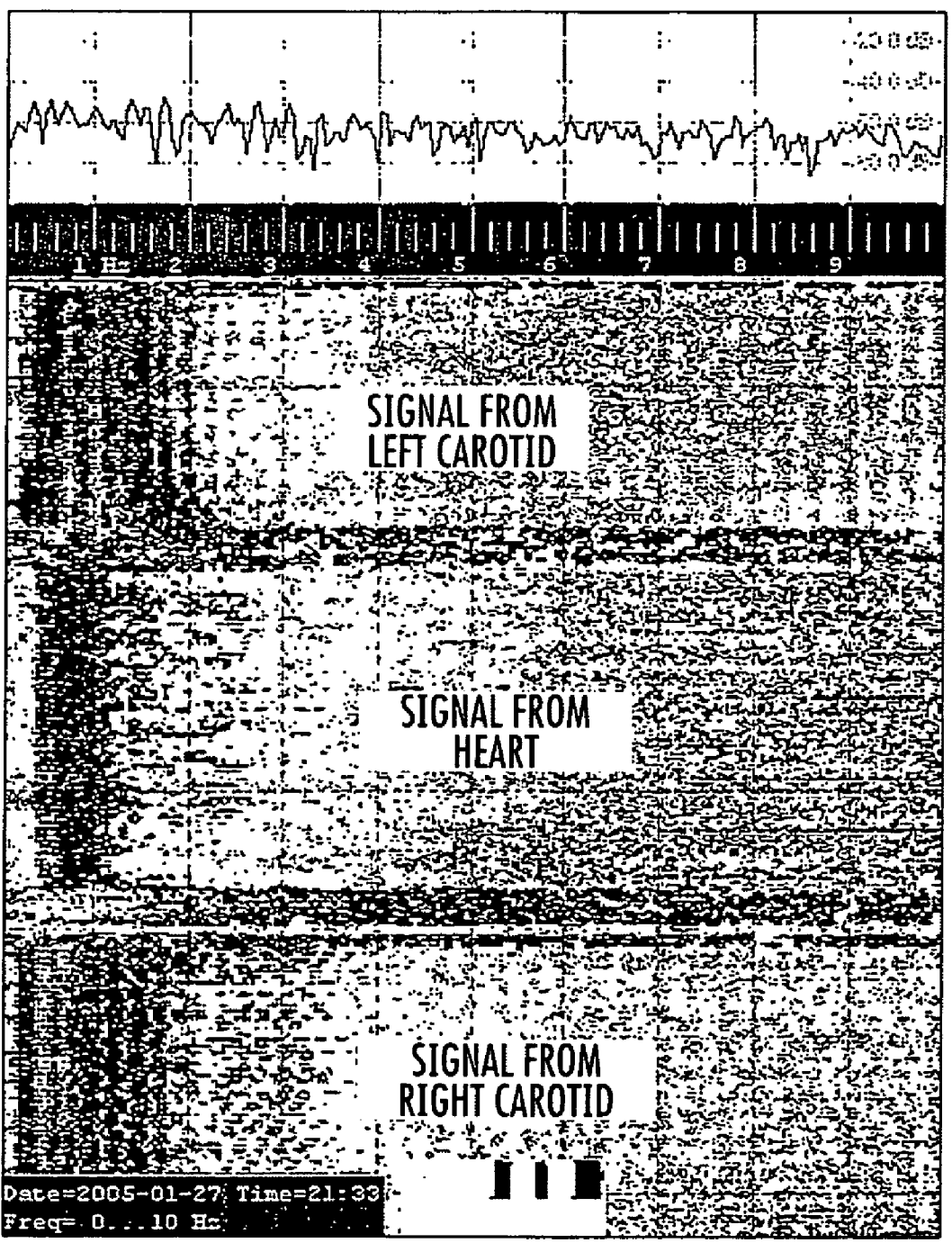
FIG. 17 is a graph of the frequency analysis for the left carotid (top), heart (middle) and right carotid (bottom) in the low, inaudible frequency range 0-10 Hz for an adult.

This result can have a large range depending on the values of the parameters but typical readings will be between 1 Hz to 10 Hz corresponding to ULF waves. FIG. 17 shows that there are many low frequencies bands in the 0.01 Hz to 10 Hz range that do not come from the heart. FIG. 17 is a graph of the frequency analysis for the left carotid (top), heart (middle) and right carotid (bottom) in the low, inaudible frequency range 0-10 Hz for an adult. The dark vertical lines indicate frequencies detected in the 0-10 Hz range. As can be seen in FIG. 17, there is a clear difference between the three recordings. The analysis shows that the heart frequencies are more closely packed near ~1.5 Hz (65 beats per minute) and that the carotid arteries radiate distinct frequency bands. The frequencies are due to geometry and distance from the pressure source, which is the heart. There is also an asymmetry between the right and left carotid arteries, possibly indicating more stenosis on one side.

Therefore, for arterial blood flow in patients with some form of arterial disease, many low frequency phenomena ranging from 0.01 to about 300 Hz may be observed, far lower than the frequencies used in ultrasound. The lowest part of the frequency range is important, in the range of 0.01 to 20 Hz, which is generally below audible sound, based on preliminary experimental results (for example, FIG. 17 shows features in the range from 0 to 10 Hz). These frequencies can be related to various parameters, some which can be determined clinically, such as $v_0$, $U_0$, Re etc. Others parameters, which are "health parameters", can be determined from the sound waves, such as h, κ, $r_0$ etc. Regions in the health-parameter space may be established which will produce different sound signals.

EXAMPLE 4

Sample Numerical Analysis of Line-Perturbation Model

Figures 11A, 11B, 11C:
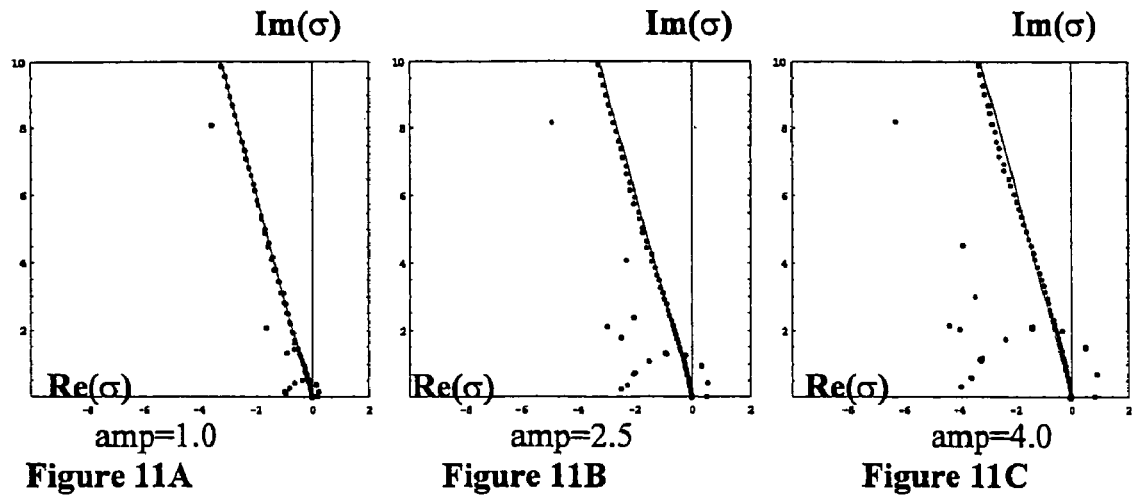
FIGS. 11A-11C are graphs of resonance frequencies σ as a function of θ for amplitudes (amp=κ/2 m) of 1.0, 2.5 and 4.0 units, respectively, in a channel of width 8.0 units according to embodiments of the present invention.

Calculations using Equation (2.9a) in Example 2 and Equation (3.4) in Example 3 (the case of a line-perturbation) were performed and graphed in FIGS. 11A-11C, 12A-12C, 13A-13C, 14A-14C, 15A-15D and 16A-16B. Features in the graphs in FIGS. 11A-11C, 12A-12C, 13A-13C, 14A-14C, 15A-15D and 16A-16B that may be used to identify the perturbations as line-perturbations include points that lie substantially on ellipses. It should be understood that, although the graphs in FIGS. 11A-11C, 12A-12C, 13A-13C, 14A-14C, 15A-15D and 16A-16B are in two coordinates, calculations may be performed in all four coordinates in certain embodiments of the present invention. The oscillations corresponding to line-perturbations have four main features: i) The straight lines with many points in correspond to the continuous spectrum, which generally does not play a part in localized oscillations. In the frequency analysis of real in vivo recordings, these straight lines may not be present. However, moving the continuous spectrum by an angle θ in the theoretical analysis can reveal localized spectrum, or resonances that are illustrated by the straight lines illustrated in the graphs of FIGS. 11A-11C, 12A-12C, 13A-13C, 14A-14C, 15A-15D and 16A-16B; ii) Bound states (not shown) may be present as points on the Re(σ) axis. These points also may not be observed, except with ultra sound or other techniques, because they are bound to the perturbation. Hence, they generally do not flow downstream; iii) Inner ellipses (or spirals) with many points that occur at substantially regular intervals, as predicted by equation (2.11a) of Example 2. Half of the ellipse is shown in two coordinates in FIGS. 11A-11C, 12A-12C, 13A-13C, 14A-14C, 15A-15D and 16A-16B centered around the origin. Such a regular pattern is expected for line perturbations, but not for point perturbations. FIGS. 11A-11C show a dramatic increase in the radius of the ellipse as amplitude or "amp" (amp=κ/2 m) increases. iv) Finally, there are "scattered points", for example, as indicated in FIGS. 13A-13C, which are different for different "m" values. The scattered points may also lie substantially on an ellipse or spiral. As illustrated, the scattered points are spaced apart so that the ellipses on which the scattered points lie are generally not visible in the two coordinates that are graphed. The ellipses may be visible in a graph of all four coordinates. The scattered points are circled in FIGS. 12A-12C, 14A-14C, and 15A-15D. The correspondence between the scattered points and line perturbation follows from numerical solutions of the problem, as displayed FIGS. 11A-11C, 12A-12C, 13A-13C, 14A-14C, 15A-15D and 16A-16B.

Figures 12A, 12B, 12C:
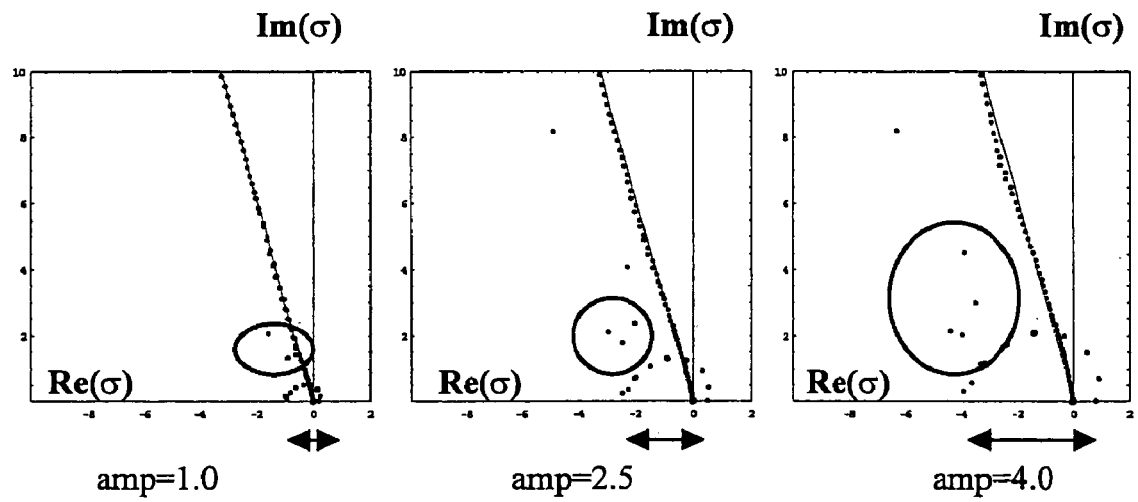
FIGS. 12A-12C are graphs of resonance frequencies according to embodiments of the present invention for amplitudes 1.0, 2.5 and 4.0 units, respectively. Some of the features dependent on amplitude are circled.
Figure 15A:
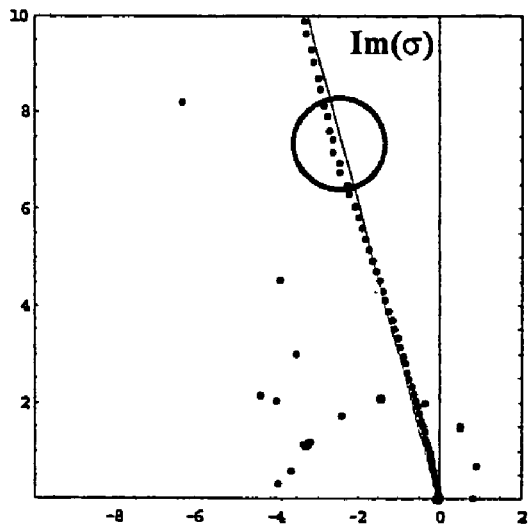
FIGS. 15A-15D are graphs of resonance frequencies as a function of θ for complex-scaling angles of π/5.0, π/4.8, π/4.6, π/4.4, respectively, according to embodiments of the present invention.
Figure 15B:
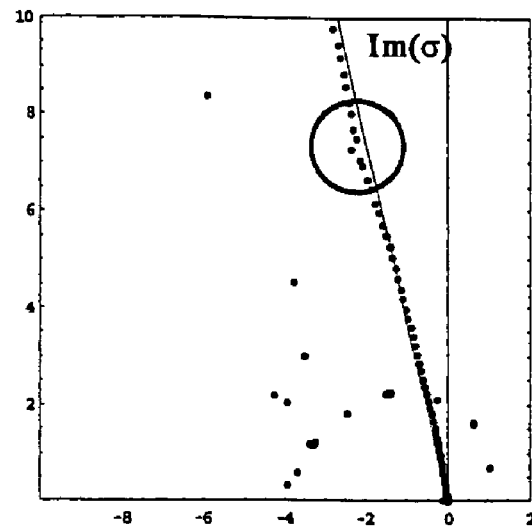
Figure 15C:
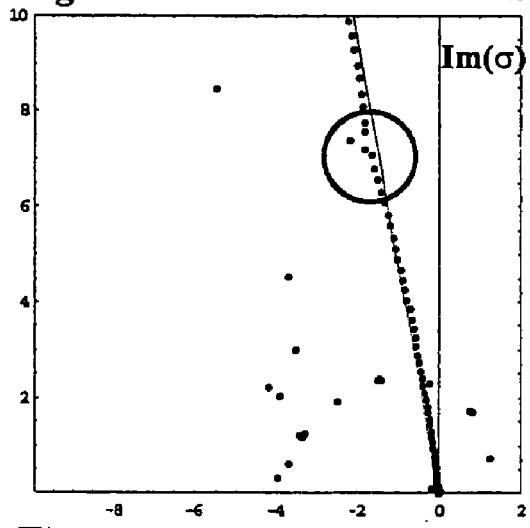
Figure 15D:
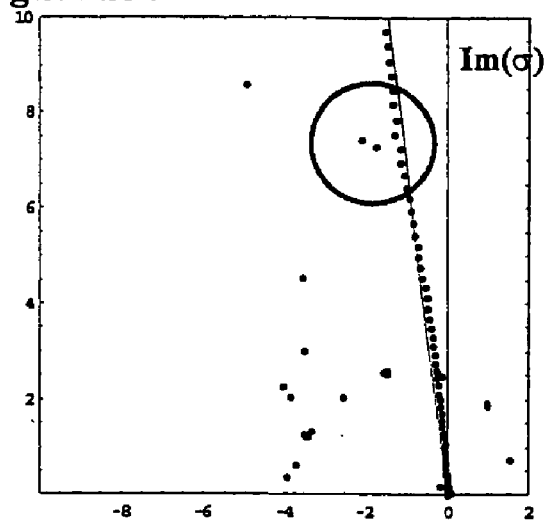

FIGS. 11A-11C are graphs of resonance frequencies plotted in a complex-frequency grid for a perturbation having amplitude or amp values of 1.0, 2.5, and 4.0 units (amp=κ/2 m) in a channel having a width of 8.0 units. As illustrated in FIGS. 11A-11C, the number of resonances increases for greater amps and the "radius" of the resonance ellipse increases at greater amps. FIGS. 12A-12C includes circles around those points in FIGS. 11A-11C which are more dramatically changed by changing the amp parameter. This indicates that there can be discernable signatures in the complex-frequency grid for determining this shape parameter. FIGS. 11A-11C and 12A-12C each use the following parameters, which may be typical of flow through a channel having a relatively small line-perturbation:

ξbasis=70: the number of basis functions in the ξ direction;
ηbasis=5: the number of basis functions in the η direction;
ξlen=32: the length of the channel (in units);
ηlen=4: the half width of the channel (in units);
m=0.5, 1.0, 1.5 (FIGS. 11A-11C, respectively and FIGS. 12A-12C, respectively): the reciprocal of variance parameter:
λ=1: scale parameter (not frequency in the program), has fixed value 1;

The λlen is much longer than the width, essentially infinite in length. The ηlen corresponds to the half width h and changing this value only changes the scale of the frequencies. From (3.4) in Example 2 the first radius (l=0) depends on $(Re/2h)^2$, however in the computer program $(Re/2h)^2$ depends on amp. The program uses a change of variables so that, $$-i\lambda_0 h^2 e^{2m} = \sigma + (Re/2)^2 - 1 - \text{amp}$$

(Note λ is a scale parameter of the program, but $\lambda_0$ is the frequency in the theoretical model, and σ is the frequency in the program and illustrated in the FIGS. 11A-11C, 12A-12C, 13A-13C, 14A-14C, 15A-15D and 16A-16B). Thus, in this example, a larger Re (Reynolds number) corresponds to a larger radius for the ellipse of points, and a higher frequency is produced/detected. However, a larger width (2h) corresponds to a smaller radius, which also corresponds to a lower frequency. The dependence on "m" is more complicated and is heuristically given by solutions of (2.9a) in Example 2. The calculations in this example have been simplified and use Equation 3.4 in Example 3.

FIGS. 13A-13C are graphs of resonance frequencies for a reciprocal variance value, m, of 1.5, 1.0, and 0.5. FIGS. 14A-14C contain circles around those points which are more dramatically changed by changing m. This indicates that there may be many discernable signatures in the complex-frequency grid for determining this shape parameter. FIGS. 13A-13C and 14A-14C each use the following parameters, which may be typical of flow through a channel having a relatively small line-perturbation: ξbasis=70; ηbasis=5; ξlen=32; ηlen=3; and amp=1.0. Using this in equation (3.4) of Example 3, a radius of about 1.0 can be calculated, as is clearly seen by the ellipse in FIG. 11A. As used in this example, the "radius" refers to the distance between the origin (or center of the ellipse) and the intersection of the ellipse with the $-\text{Re}(\sigma)$ axis. FIGS. 15A-15D are graphs of resonance frequencies for complex-scaling angles $\theta=\pi/5.0, \pi/4.8, \pi/4.6, \pi/4.4$. As can be seen in FIGS. 15A-15D, the analysis with respect to the θ parameter is generally stable, i.e., the resonance values do not change significantly with changes in θ. The resonances are substantially stationary as the line of frequencies moves, but new resonances can be seen by analyzing larger θ. The lack of motion of the resonances due to changes in angle may be evidence that the described calculations may be statistically robust, computationally stable and diagnostically dependable. FIGS. 15a-15D each use the following parameters, which may be typical of flow through a channel having a relatively small line-perturbation: ξbasis=70; ηbasis=5; λ=1; ξlen=32; hlen=4; amp=4.0; and m=1. Using this in equation (3.4) of Example 3 gives a radius of about 4.0, as is clearly seen by the ellipse in FIG. 11C.

FIGS. 16A-16B are graphs of a bump perturbation, i.e. κ>0 (FIG. 16A), and an aneurism perturbation, i.e. κ<0 (FIG. 16B), derived using a numerical simulation of complex-scaling methods. The features in FIG. 16B are reduced as compared with FIG. 16A. In particular, the size of the ellipse is smaller in FIG. 16B; however there are two resonances that are very clear, thus a distinction between the bump perturbation and an aneurism is suggested. FIG. 16A illustrates a bump perturbation having the following values: amp=0.5 and m=1; and FIG. 16B illustrates an anueurism perturbation having the following values: amp=−0.5; and m=1. The elliptical patterns in FIGS. 16A-16B both use the following parameters: ξbasis=70; ηbasis=5; λ=1; ξlen=32; ηlen=11; θ=π/4.3. Here again, from Example 3, equation (3.4) the ellipse radius is about 0.5, as seen in FIG. 16A, which is the value of amp. For the aneurism case the ellipse is greatly reduced for the same size perturbation, indicating more difficulty in detecting this anomaly in this case.

The foregoing embodiments are illustrative of the present invention, and are not to be construed as limiting thereof. The invention is defined by the following claims, with equivalents of the claims to be included therein.

That which is claimed is:

1. A non-invasive method of detecting arterial disease in vivo, comprising:
obtaining acoustic signals from one or more sensors held on an external body region proximate at least one artery;
generating a complex frequency grid of frequencies and associated lifetimes of the obtained acoustic signals;
providing a predictive model of complex frequencies associated with peak-perturbation acoustic signals attributed to boundary perturbations in vivo that occur with early stage arterial disease;
providing a predictive model of complex frequencies associated with line-perturbation acoustic signals attributed to boundary perturbations in vivo that occur with later stage arterial disease; and
determining whether peak and/or line-perturbation acoustic signals of the predictive models are present to detect whether the subject has arterial disease, wherein the arterial disease is selected from the group consisting of plaque, deposits, stenosis, occluded, obstructed blood flow, arterial hardening, arterial wall thickness perturbations, thickening of arterial junctions, emboli, blood clots, aneurysms and combination thereof.

2. A method according to claim 1, wherein the generating step comprises:
generating a frequency scatter-plot of data corresponding to the obtained acoustic signals in the complex frequency grid; and wherein the determining step assesses whether any of the generated complex frequencies lie substantially in ellipses with a plurality of frequencies on each ellipse to determine the presence of line-perturbations.

3. A method according to claim 1, wherein the generating step comprises generating a frequency scatter-plot of data corresponding to the obtained acoustic signals in the complex frequency grid; and wherein the determining step assesses whether the generated complex frequencies are isolated complex frequencies of low frequency to determine the presence of peak-perturbations.

4. A method according to claim 1, wherein the obtaining step comprises detecting acoustic signals associated with the carotid artery of a subject using one or more external sensors.

5. A method according to claim 4, wherein the one or more external sensors are on a cuff configured for placement on the subject's neck.

6. A method according to claim 1, wherein providing a predictive model of complex frequencies associated with peak-perturbation acoustic signals comprises determining eigenfunctions corresponding to characteristic peak-perturbations of flow through the artery.

7. A method according to claim 6, wherein the determining step comprises identifying frequencies and associate lifetimes from the frequency grid and identifying eigenvalues corresponding to the eigenfunctions based on the identified frequencies and associated frequency lifetimes.

8. A method according to claim 7, further comprising characterizing the condition of the artery based on the eigenvalues.

9. A method according to claim 7, wherein identifying eigenvalues corresponding to the eigenfunctions comprises determining a pattern of resonance frequencies.

10. A method according to claim 9, wherein determining a pattern of resonance frequencies comprises determining ratios of the resonance frequencies.

11. A method according to claim 10, wherein determining a pattern of resonance frequencies for uniform flow speed is $U_0$ in a blood vessel of width h, for blood having a viscosity $v_0$ for a simple boundary perturbation with peak curvature κ, comprises identifying a family of complex frequencies having the formula:

$$f \sim 0.212 \kappa U_0 - 5.35 v_0 \kappa^2.$$

12. A method according to claim 7, wherein the eigenfunctions comprise a complex scaling applied to a conformal transformation of the Navier-Stokes equation:

$$\partial_t \vec{q} + \vec{q}\cdot\vec{\nabla}\vec{q} = -\rho_0^{-1}\vec{\nabla}p + v_0\nabla^2\vec{q}, \vec{\nabla}\cdot\vec{q} = 0,.$$

13. A method according to claim 1, wherein providing a predictive model of complex frequencies associated with line-perturbation acoustic signals comprises determining eigenfunctions corresponding to characteristic line-perturbations of flow through the artery.

14. A method according to claim 13, wherein the determining step comprises identifying frequencies and associate lifetimes from the frequency grid and identifying eigenvalues corresponding to the eigenfunctions based on the identified frequencies and associated frequency lifetimes.

15. A method according to claim 14, further comprising characterizing the condition of the artery based on the eigenvalues.

16. A method according to claim 14, wherein identifying eigenvalues corresponding to the eigenfunctions comprises determining a pattern of resonance frequencies.

17. A method according to claim 16, wherein determining a pattern of resonance frequencies comprises determining ratios of the resonance frequencies.

18. A method according to claim 17, wherein determining a pattern of resonance frequencies for uniform flow $U_0$ in a blood vessel of width h, for blood having a viscosity $v_0$ for a simple boundary perturbation with peak curvature κ, comprises identifying a family of complex frequencies having the formula:

$$f_n \sim \lambda_0 v_0 \exp[i\beta_n]$$

where the frequency radius is: $\lambda_0 = (U_0/2v_0)^2 \exp[-2(h\kappa)/3]$ and the angles are: $\beta_n = 2 \arccos[(v_0(h\kappa)^{1/2}/U_0 h)(2n+1)]$ for n=0, 1, 2, ... M.

19. A method according to claim 1, wherein the determining step comprises identifying an occlusion in a blood vessel.

20. A method according to claim 19, further comprising identifying a location of the occlusion.

21. A method according to claim 19, further comprising identifying a size of the occlusion.

22. A method according to claim 19, further comprising identifying a rigidity of the occlusion.

23. A method according to claim 1, wherein the determining step comprises identifying an aneurism in the blood vessel.

24. A method according to claim 1, further comprising providing a driving acoustic signal to the blood vessel.

25. A method according to claim 24, further comprising detecting changes between the detected acoustic signal and the driving acoustic signal.

26. A non-invasive system for detecting arterial disease in vivo, comprising:
one or more acoustic signal sensors configured for positioning on an external body region proximate at least one artery for obtaining acoustic signals;
a complex frequency data point generator module configured to generate a complex frequency grid of frequencies and associated lifetimes using the obtained acoustic signals;
a peak-perturbation module in communication with the complex frequency data point generator comprising a predictive model of complex frequencies associated with peak-perturbation acoustic signals attributed to boundary perturbations in vivo that occur with early stage arterial disease;
a line-perturbation module in communication with the complex frequency data point generator comprising a predictive model of complex frequencies associated with line-perturbation acoustic signals attributed to boundary perturbations in vivo that occur with later stage arterial disease and/or acoustic signals attributed to junction perturbations where arteries split in vivo; and
the peak-perturbation module and the line-perturbation module being configured for determining whether peak and/or line-perturbation acoustic signals of the predictive models are present to detect whether the subject has arterial disease, wherein the arterial disease is selected from the group consisting of plaque, deposits, stenosis, occluded, obstructed blood flow, arterial hardening, arterial wall thickness perturbations, thickening of arterial junctions, emboli, blood clots, aneurysms and combination thereof.

27. A computer program product for detecting arterial disease in vivo, the computer program product comprising program code embodied in a computer-readable storage medium, the computer program code comprising:
computer program code that is configured to obtain acoustic signals from one or more sensors held on an external body region proximate at least one artery;
computer program code that is configured to generate a complex frequency grid of frequencies and associated lifetimes of the obtained acoustic signals;
computer program code that is configured to provide a predictive model of complex frequencies associated with peak-perturbation acoustic signals attributed to boundary perturbations in vivo that occur with early stage arterial disease;
computer program code that is configured to provide a predictive model of complex frequencies associated with line-perturbation acoustic signals attributed to boundary perturbations in vivo that occur with later stage arterial disease ardor the thickening of arterial junctions; and
computer program code that is configured to determine whether peak and/or line-perturbation acoustic signals of the predictive models are present to detect whether the subject has arterial disease, wherein the arterial disease is selected from the group consisting of plaque, deposits, stenosis, occluded, obstructed blood flow, arterial hardening, arterial wall thickness perturbations, thickening of arterial junctions, emboli, blood clots, aneurysms and combination thereof.

28. A method according to claim 1, wherein the predictive model of complex frequencies associated with peak-perturbation acoustic signals is based on laminar flow.

29. A system according to claim 26, wherein the predictive model of complex frequencies associated with peak-perturbation acoustic signals is based on laminar flow.

30. A computer program product according to claim 27, wherein the predictive model of complex frequencies associated with peak-perturbation acoustic signals is based on laminar flow.

* * * * *